US012636319B2

(12) United States Patent
Seo et al.

(10) Patent No.: US 12,636,319 B2
(45) **Date of Patent: *May 26, 2026**

(54) **PHARMACEUTICAL COMPOSITION FOR PREVENTING OR TREATING ATOPIC DISEASE CONTAINING *AKKERMANSIA MUCINIPHILA* STRAIN**

(71) Applicant: ENTEROBIOME INC., Goyang-si (KR)

(72) Inventors: Jae-Gu Seo, Gimpo-si (KR); Joo-Hyun Shin, Seoul (KR); Dokyung Lee, Seoul (KR); Yoonmi Lee, Goyang-si (KR); Seo Yul Jang, Goyang-si (KR); Hye Rim Byeon, Paju-si (KR)

(73) Assignee: ENTEROBIOME INC., Goyang-si (KR)

( * ) Notice: Subject to any disclaimer, the term of this patent is extended or adjusted under 35 U.S.C. 154(b) by 1017 days.

This patent is subject to a terminal disclaimer.

(21) Appl. No.: 17/430,010

(22) PCT Filed: Feb. 26, 2021

(86) PCT No.: PCT/KR2021/002432
§ 371 (c)(1),
(2) Date: Aug. 11, 2021

(87) PCT Pub. No.: WO2022/045501
PCT Pub. Date: Mar. 3, 2022

(65) Prior Publication Data
US 2023/0136694 A1     May 4, 2023

(30) Foreign Application Priority Data
Aug. 26, 2020    (KR) ........................ 10-2020-0107617

(51) Int. Cl.
| | |
|---|---|
| *A61K 35/74* | (2015.01) |
| *A61K 45/06* | (2006.01) |
| *A61K 47/55* | (2017.01) |
| *A61P 17/00* | (2006.01) |

(52) U.S. Cl.
CPC .............. *A61K 35/74* (2013.01); *A61K 45/06* (2013.01); *A61K 47/551* (2017.08); *A61P 17/00* (2018.01)

(58) Field of Classification Search
CPC ........ A61P 17/00; A61K 35/74; A61K 47/551
See application file for complete search history.

(56) References Cited

U.S. PATENT DOCUMENTS

| | | |
|---|---|---|
| 10,537,597 B2 | 1/2020 | O'Mahony et al. |
| 2018/0264053 A1 | 9/2018 | Lynch et al. |
| 2020/0164003 A1* | 5/2020 | O'Mahony .......... A61K 9/0053 424/93.4 |

FOREIGN PATENT DOCUMENTS

| | | |
|---|---|---|
| KR | 10-2013-0034764 A | 4/2013 |
| KR | 10-2016-0053447 A | 5/2016 |
| KR | 10-2016-0069733 A | 6/2016 |
| KR | 10-1667496 B1 | 10/2016 |
| KR | 10-1925135 B1 | 12/2018 |
| KR | 10-2128287 B1 | 6/2020 |
| KR | 10-2128289 B1 | 6/2020 |
| KR | 10-2185827 B1 | 12/2020 |
| WO | 2020/040407 A1 | 2/2020 |

OTHER PUBLICATIONS

Nucleotide [Internet]. Bethesda (MD): National Library of Medicine (US), National Center for Biotechnology Information; Accession No. CP025834.1, Akkermansia muciniphila strain EB-AMDK-19 chromosome, complete genome. Available from: https://www.ncbi.nlm.nih.gov/nuccore/CP025834.1; Accessed Jun. 7, 2024. (Year: 2019).*
Amor et al., "The use of cyclosporine in dermatology: Part I", Journal of the American Academy of Dermatology, vol. 63(6), pp. 925-946 (Year: 2010).*
Kim et al., "Akkermansia muciniphila Prevents Fatty Liver Disease, Decreases Serum Triglycerides, and Maintains Gut Homeostasis", Applied and Environmental Microbiology, vol. 86(7), pp. 1-9. (Year: 2020).*
Kim et al., "Microbiome of the Skin and Gut in Atopic Dermatitis (AD): Understanding the Pathophysiology and Finding Novel Management Strategies", Journal of Clinical Medicine, vol. 8, Article 444, pp. 1-23. (Year: 2019).*
Tiina Drell et al., "Differences in Gut Microbiota Between Atopic and Healthy Children", Curr Microbiol, 2015, pp. 177-183, vol. 71.
Ting Zhang et al., "Akkermansia muciniphila is a promising probiotic", Microbial Biotechnology, 2019, pp. 1109-1125, vol. 12.
International Searching Authority, International Search Report of PCT/KR2021/002432 dated Jun. 3, 2021 [PCT/ISA/210].
International Searching Authority, Written Opinion of PCT/KR2021/002432 dated Jun. 3, 2021 [PCT/ISA/237].
Extended European Search Report dated May 10, 2023 in Application No. 21762586.2.

* cited by examiner

*Primary Examiner* — Melenie L Gordon
*Assistant Examiner* — Grant C Currens
(74) *Attorney, Agent, or Firm* — Sughrue Mion, PLLC

(57) ABSTRACT

A pharmaceutical composition containing an *Akkermansia muciniphila* EB-AMDK19 strain or a culture or dried product thereof and uses thereof are disclosed. The composition is effective for the prevention or treatment of atopic disease. The pharmaceutical composition exhibits a preventive or therapeutic effect on atopic disease at the same level as that of steroid-based drugs, and thus is not only promising as pharmabiotics, but also useful in the development of food and cosmetics.

12 Claims, 20 Drawing Sheets
Specification includes a Sequence Listing.

[a]*Streptococcus pyogenes ATCC 19615 (β-hemolysis)*

FIG.12

DEX-positive control group

DNCB-induced group

Normal

EB-AMDK19

BAA-835

X200
Hyperkeratosis(arrowhead)
Hyperplasia(arrow)

Hyperkeratosis

Hyperplasia

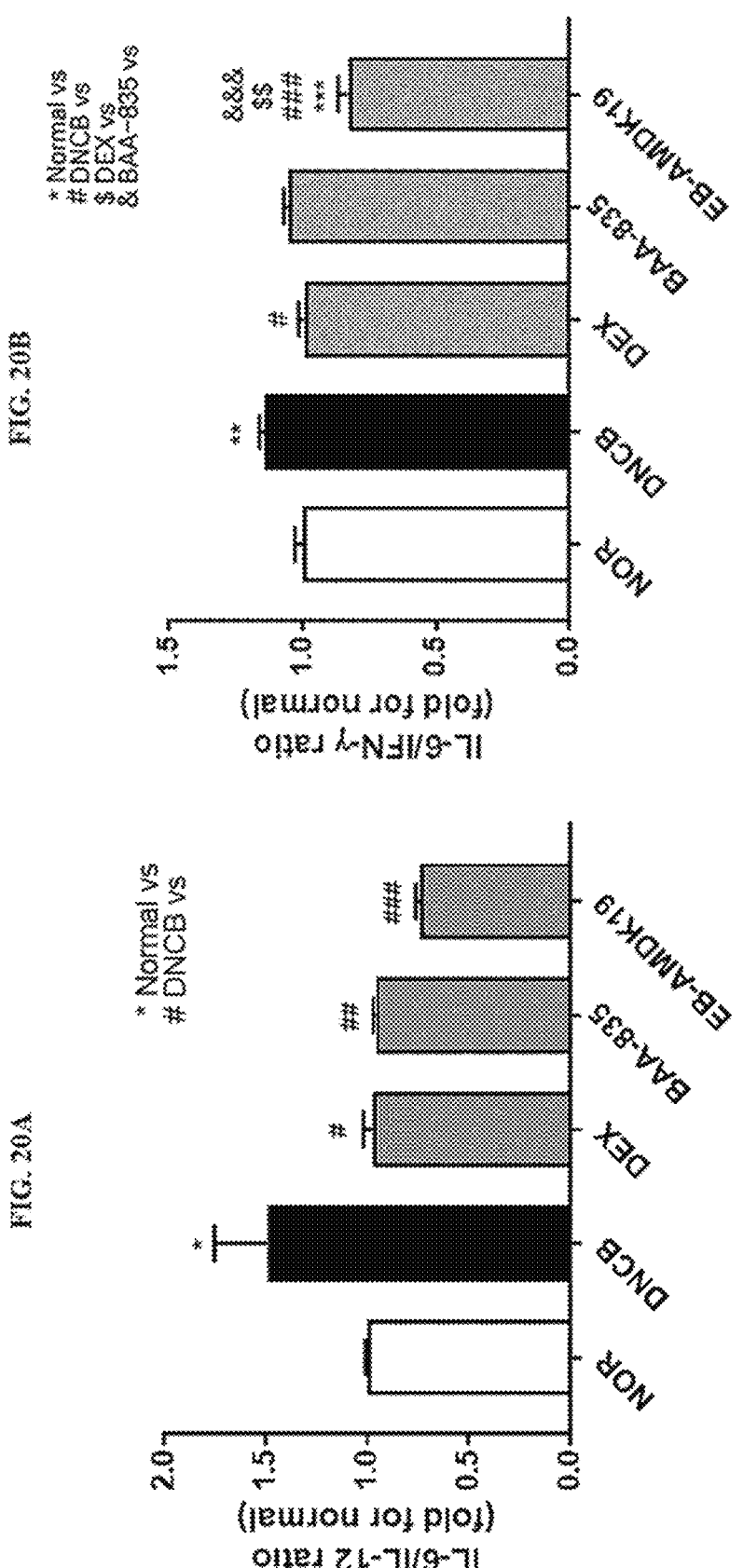

SEQUENCE LISTING

```
<160> NUMBER OF SEQ ID NOS: 8

<210> SEQ ID NO 1
<211> LENGTH: 1464
<212> TYPE: DNA
<213> ORGANISM: Akkermansia muciniphila
<220> FEATURE:
<223> OTHER INFORMATION: 16s rRNA of Akkermansia muciniphila EB-AMDK19
      strain (KCTC13761BP)

<400> SEQUENCE: 1
aacgaacgct ggcggcgtgg ataagacatg caagtcgaac gagagaattg ctagcttgct      60
aataattctc tagtggcgca cgggtgagta acacgtgagt aacctgcccc cgagagcggg     120
atagccctgg gaaactggga ttaataccgc atagtatcga aagattaaag cagcaatgcg     180
cttggggatg ggctcgcggc ctattagtta gttggtgagg taacggctca ccaaggcgat     240
gacgggtagc cggtctgaga ggatgtccgg ccacactgga actgagacac ggtccagaca     300
cctacgggtg gcagcagtcg agaatcattc acaatggggg aaaccctgat ggtgcgacgc     360
cgcgtggggg aatgaaggtc ttcggattgt aaacccctgt catgtgggag caaattaaaa     420
agatagtacc acaagaggaa gagacggcta actctgtgcc agcagccgcg gtaatacaga     480
ggtctcaagc gttgttcgga atcactgggc gtaaagcgtg cgtaggctgt ttcgtaagtc     540
gtgtgtgaaa ggcgcgggct caacccgcgc acggcacatg atactgcgag actagagtaa     600
tggaggggga accggaattc tcggtgtagc agtgaaatgc gtagatatcg agaggaacac     660
tcgtggcgaa ggcgggttcc tggacattaa ctgacgctga ggcacgaagg ccaggggagc     720
gaaagggatt agataccct gtagtcctgg cagtaaacgg tgcacgcttg gtgtgcgggg      780 aatcgaccc ctgcgtgccg gagctaacgc gttaagcgtg ccgcctgggg agtacggtcg      840
caagattaaa actcaaagaa attgacgggg acccgcacaa gcggtggagt atgtggctta      900
attcgatgca acgcgaagaa ccttacctgg gcttgacatg taatgaacaa catgtgaaag     960
catgcgactc ttcggaggcg ttacacaggt gctgcatggc cgtcgtcagc tcgtgtcgtg    1020
agatgtttgg ttaagtccag caacgagcgc aacccctgtt gccagttacc agcacgtgaa    1080
ggtggggact ctggcgagac tgcccagatc aactgggagg aaggtgggga cgacgtcagg    1140
tcagtatggc ccttatgccc agggctgcac acgtactaca atgcccagta cagaggggc     1200 cgaagccgcg aggcggagga aatcctgaaa actgggccca gttcggactg taggctgcaa    1260
cccgcctaca cgaagccgga atcgctagta atggcgcatc agctacggcg ccgtgaatac    1320
gttcccgggt cttgtacaca ccgcccgtca catcatggaa gccggtcgca cccgaagtat    1380
ctgaagccaa ccgcaaggag gcagggtcct aaggtgagac tggtaactgg gatgaagtcg    1440
taacaaggta gccgtagggg aacc                                          1464

<210> SEQ ID NO 2
```

```
<211> LENGTH: 20
<212> TYPE: DNA
<213> ORGANISM: Artificial Sequence
<220> FEATURE:
<223> OTHER INFORMATION: AM1 primer forward

<400> SEQUENCE: 2
cagcacgtga aggtgggggac                                          20

<210> SEQ ID NO 3
<211> LENGTH: 20
<212> TYPE: DNA
<213> ORGANISM: Artificial Sequence
<220> FEATURE:
<223> OTHER INFORMATION: AM2 primer revere

<400> SEQUENCE: 3
ccttgcggtt ggcttcagat                                          20

<210> SEQ ID NO 4
<211> LENGTH: 22
<212> TYPE: DNA
<213> ORGANISM: Artificial Sequence
<220> FEATURE:
<223> OTHER INFORMATION: ERIC-1 primer Forward

<400> SEQUENCE: 4
atgtaagctc ctggggattc ac                                       22

<210> SEQ ID NO 5
<211> LENGTH: 22
<212> TYPE: DNA
<213> ORGANISM: Artificial Sequence
<220> FEATURE:
<223> OTHER INFORMATION: ERIC-2 primer Reverse

<400> SEQUENCE: 5
aagtaagtga ctggggtgag cg                                       22

<210> SEQ ID NO 6
<211> LENGTH: 15
<212> TYPE: DNA
<213> ORGANISM: Artificial Sequence
<220> FEATURE:
<223> OTHER INFORMATION: (GTG)5 Forward/Reverse

<400> SEQUENCE: 6
gtggtggtgg tggtg                                               15

<210> SEQ ID NO 7
<211> LENGTH: 20
<212> TYPE: DNA
<213> ORGANISM: Artificial Sequence
<220> FEATURE:
<223> OTHER INFORMATION: 27F primer Forward

<400> SEQUENCE: 7
agagtttgat cmtggctcag                                          20

<210> SEQ ID NO 8
<211> LENGTH: 20
<212> TYPE: DNA
<213> ORGANISM: Artificial Sequence
<220> FEATURE:
<223> OTHER INFORMATION: 1541R primer Reverse
```

-continued

<400> SEQUENCE: 8
aaggaggtga tccagccgca                                                    20

PHARMACEUTICAL COMPOSITION FOR PREVENTING OR TREATING ATOPIC DISEASE CONTAINING *AKKERMANSIA MUCINIPHILA* STRAIN

CROSS REFERENCE TO RELATED APPLICATIONS

This application is a national stage application of PCT/KR2021/002432 filed Feb. 26, 2021, which claims priority from Korean Patent Application No. 10-2020-0107617 filed Aug. 26, 2020.

SEQUENCE LISTING

The content of the electronically submitted sequence listing, file name: Sequence_Listing_As_Filed.txt; size: 3,784 bytes; and date of creation: Aug. 2, 2021, filed herewith, is incorporated herein by reference in its entirety.

TECHNICAL FIELD

The present invention relates to a pharmaceutical composition for preventing or treating atopic disease, and more particularly to a pharmaceutical composition for preventing or treating atopic disease containing an *Akkermansia muciniphila* EB-AMDK19 strain as an active ingredient.

BACKGROUND ART

In a strict sense, the term "atopy" refers to a predisposition to abnormally produce IgE in response to foreign substances entering the body from the outside. Thus, the term "atopy" is not the same as the term "allergy", but these two terms are used interchangeably with substantially the same meaning. The clinical manifestations of such hypersensitivity are referred to as "atopic diseases" or "allergic diseases". Traditionally, asthma, allergic rhinitis, allergic conjunctivitis, atopic dermatitis, urticaria, anaphylaxis, and food allergy and the like are classified as atopic diseases.

Although the causes of atopic diseases known to date are not accurately identified, it is generally believed that genetic and immunological factors are involved in atopic diseases, and it is a common opinion of experts that other environmental and mental factors act to exacerbate atopic diseases. It is known that atopic diseases are not single diseases, but are multiple diseases, including atopic dermatitis, asthma and allergic rhinitis, which occur with atomic march or appear simultaneously.

Among atopic diseases, atopic dermatitis is a chronic recurrent skin disease that affects newborns or children as well known to the public and may persist until adulthood. As the main symptom of atopic dermatitis, erythematous papules and blisters with severe itching occur in the acute phase, which is the initial stage of the disease, and they progress to exudative lesions that ooze when scratched, and at this time, secondary infections often occur. As the lesions progress, excoriations and papules occur in the subacute phase, and when the chronic phase is reached, lichenification occurs in which the skin becomes thickened. Atopic patients may receive repeated emergency care and hospitalization due to frequent recurrence and worsening symptoms, and have difficulty in normal school life, social life, or work life, resulting in mental pain, which may make normal life difficult.

Since it is difficult to fundamentally cure atopic diseases and the symptoms thereof tend to be severe, symptoms of atopic diseases are controlled through appropriate treatment without aiming to cure the atopic diseases. Currently, atopic dermatitis is mainly treated by drug therapy such as steroids, antihistamines and antibiotics. The currently most widely used therapeutic agent is dexamethasone known as a steroidal drug. Steroidal drugs have excellent anti-inflammatory and immunosuppressive effects, but when they are used for a long period of time, a problem arises in that side effects such as skin weakness, systemic hormonal symptoms, and addictive symptoms occur. Antihistamines reduce itching symptoms by inhibiting the release of histamine from mast cells, but are used as a temporary measure and may cause side effects such as insomnia, anxiety and loss of appetite for a long time.

As described above, synthetic drugs have severe side effects when used for a long period of time, and thus new treatments for atopy that have no side effects while being effective against atopic diseases are needed. As new treatments for atopy without side effects, new microbial drugs are attracting attention. Accordingly, the efficacy and function of probiotics are also attracting great attention. However, how microorganisms work in the body remains a considerable challenge, and in terms of efficacy, microorganisms merely help to keep the intestinal environment healthy, and hardly appear to exhibit certain pharmaceutical efficacy. Therefore, there is an urgent need to develop next-generation pharmabiotic treatments that have proven pharmaceutical efficacy for atopic diseases which are intractable diseases.

PRIOR ART DOCUMENTS

Patent Documents
 (Patent Document 1) KR20160069733 A
 (Patent Document 2) KR20130034764 A
 (Patent Document 3) KR101925135 B

DISCLOSURE

Technical Problem

The present invention has been conceived to overcome the above-described problems, and an object of the present invention is to provide a pharmaceutical composition for preventing or treating atopic disease containing an *Akkermansia muciniphila* EB-AMDK19 strain (KCTC13761BP) as an active ingredient.

Specifically, an object of the present invention is to provide a pharmaceutical composition for preventing or treating atopic disease, the pharmaceutical composition containing an *Akkermansia muciniphila* EB-AMDK19 strain (KCTC13761BP) which is excellent in suppressing excessive secretion of the immune hypersensitivity mediator IgE and achieving a balanced regulation between Th1-type cytokine and Th2-type cytokine immune responses.

Another object of the present invention is to provide a health functional food for preventing or ameliorating atopic disease containing an *Akkermansia muciniphila* EB-AMDK19 strain (KCTC13761BP) as an active ingredient.

Still another object of the present invention is to provide a cosmetic composition for alleviating or ameliorating atopic disease containing an *Akkermansia muciniphila* EB-AMDK19 strain (KCTC13761BP) as an active ingredient.

Technical Solution

One aspect of the present invention is directed to a pharmaceutical composition for preventing or treating atopic disease, the pharmaceutical composition containing an *Akkermansia muciniphila* EB-AMDK19 strain (accession number: KCTC13761BP) or a culture or dried product of the strain.

Another aspect of the present invention is directed to a food for preventing or ameliorating atopic disease, the food containing an *Akkermansia muciniphila* EB-AMDK19 strain (KCTC13761BP) or a culture or dried product of the strain.

Still another aspect of the present invention is directed to a cosmetic composition for alleviating or ameliorating atopic disease, the cosmetic composition containing an *Akkermansia muciniphila* EB-AMDK19 strain (KCTC13761BP) or a culture or dried product of the strain.

Advantageous Effects

The pharmaceutical composition for preventing or treating atopic disease containing the *Akkermansia muciniphila* EB-AMDK19 strain as an active ingredient according to the present invention has an excellent effect of treating atopic disease, and exhibits the effect of preventing, ameliorating or treating atopic dermatitis at the same level as that of a steroidal drug.

In addition, the pharmaceutical composition for preventing or treating atopic disease containing the *Akkermansia muciniphila* EB-AMDK19 strain as an active ingredient according to the present invention is excellent in achieving a balanced regulation between Th1 and Th2 cell immune responses, and especially achieves a balanced regulation between Th1 type cytokine and Th2 type cytokine immune responses through different immunoregulatory mechanisms depending on the severity of atopic dermatitis.

In addition, the pharmaceutical composition of the present invention directly reduces the level of serum immunoglobulin IgE, which is a major factor in the onset of atopic disease, and reduces the infiltration of mast cells, eosinophils and neutrophils into dermal cells. Thus, the pharmaceutical composition may be applied to a pharmaceutical composition for preventing or treating atopic disease, a health functional food, a cosmetic composition, and the like.

DESCRIPTION OF DRAWINGS

The above and other objects, features, and advantages of the present invention will be more clearly understood from the following detailed description taken in conjunction with the accompanying drawings, in which.

4

Figure 6:
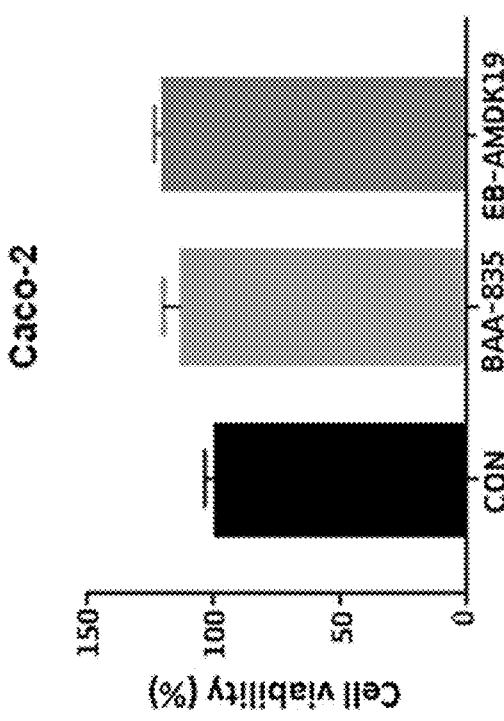
Figure 6:
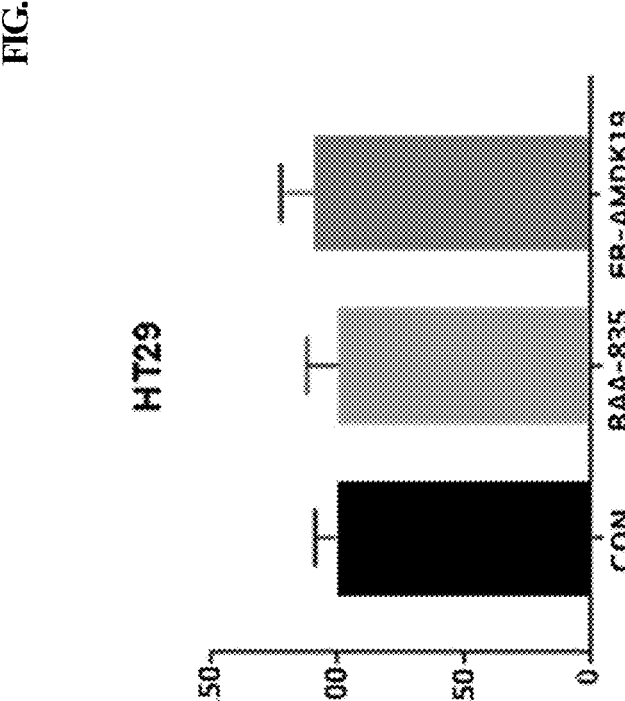
Figure 7:
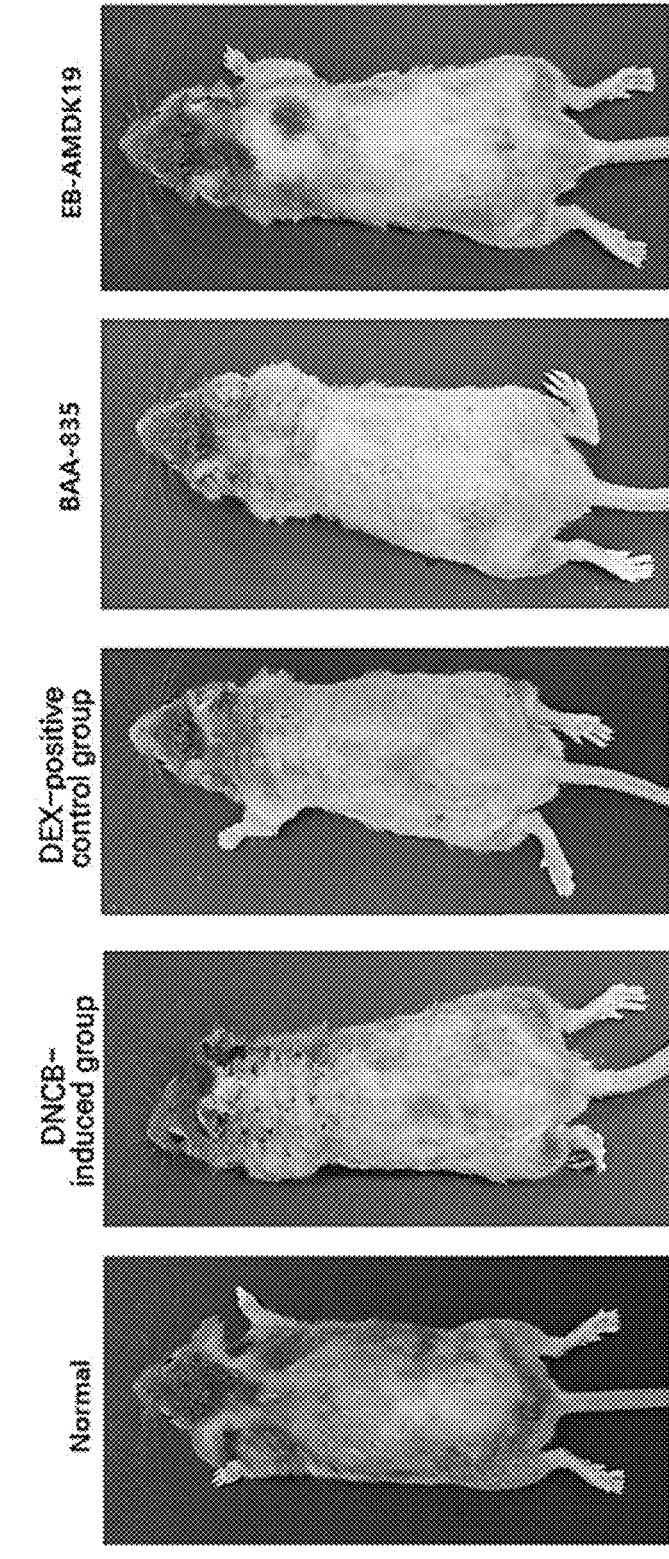
Figure 8:
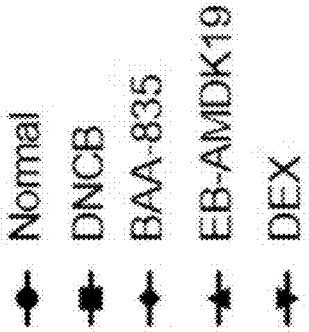
Figure 8:
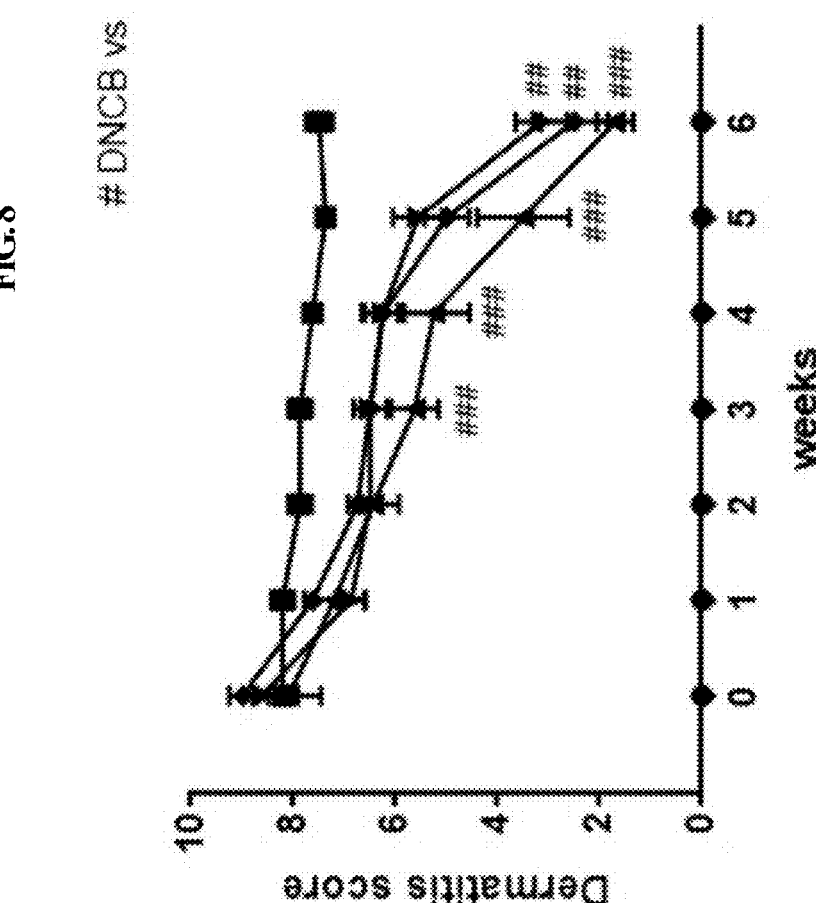
Figure 9:
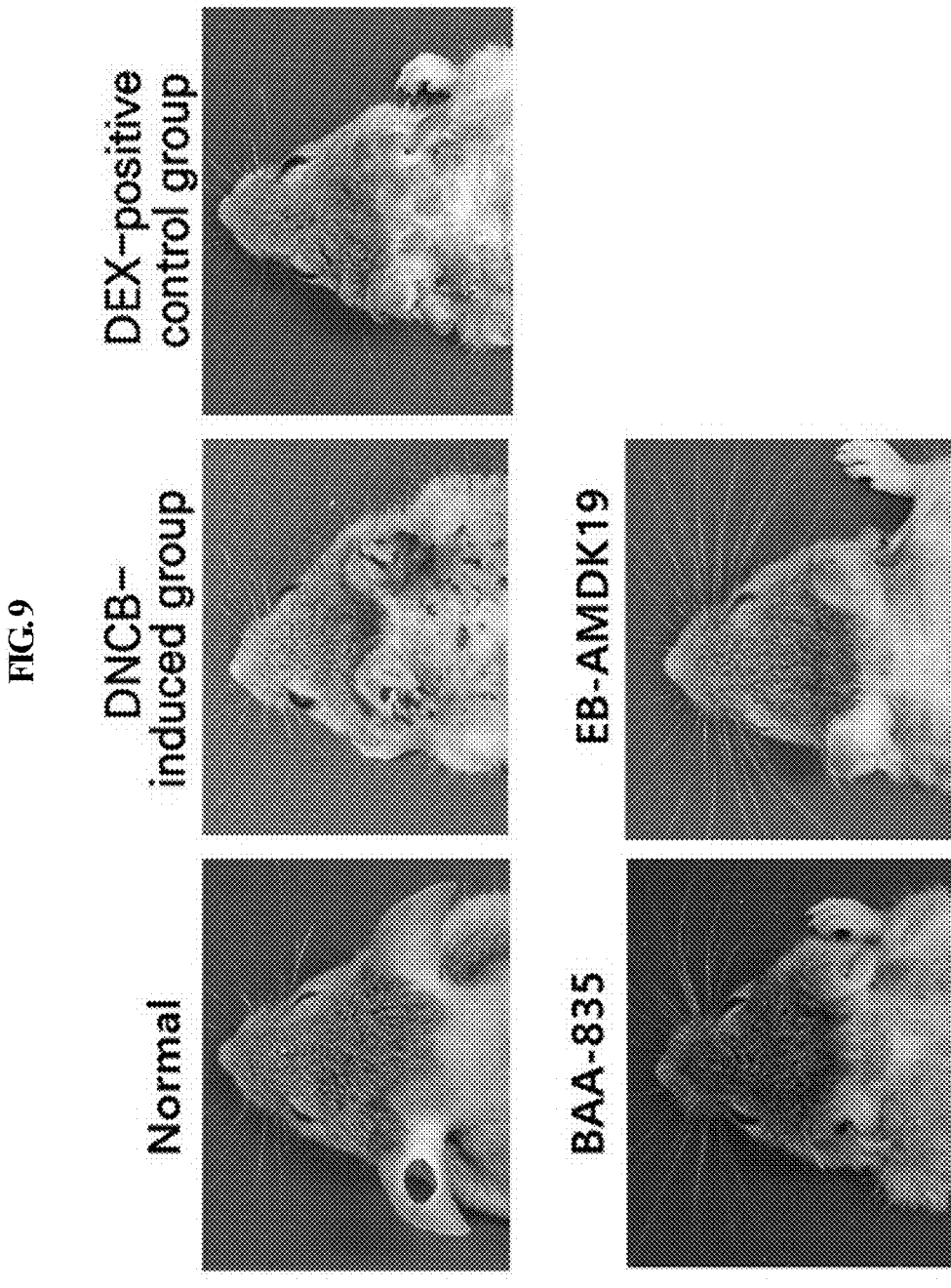
Figure 10:
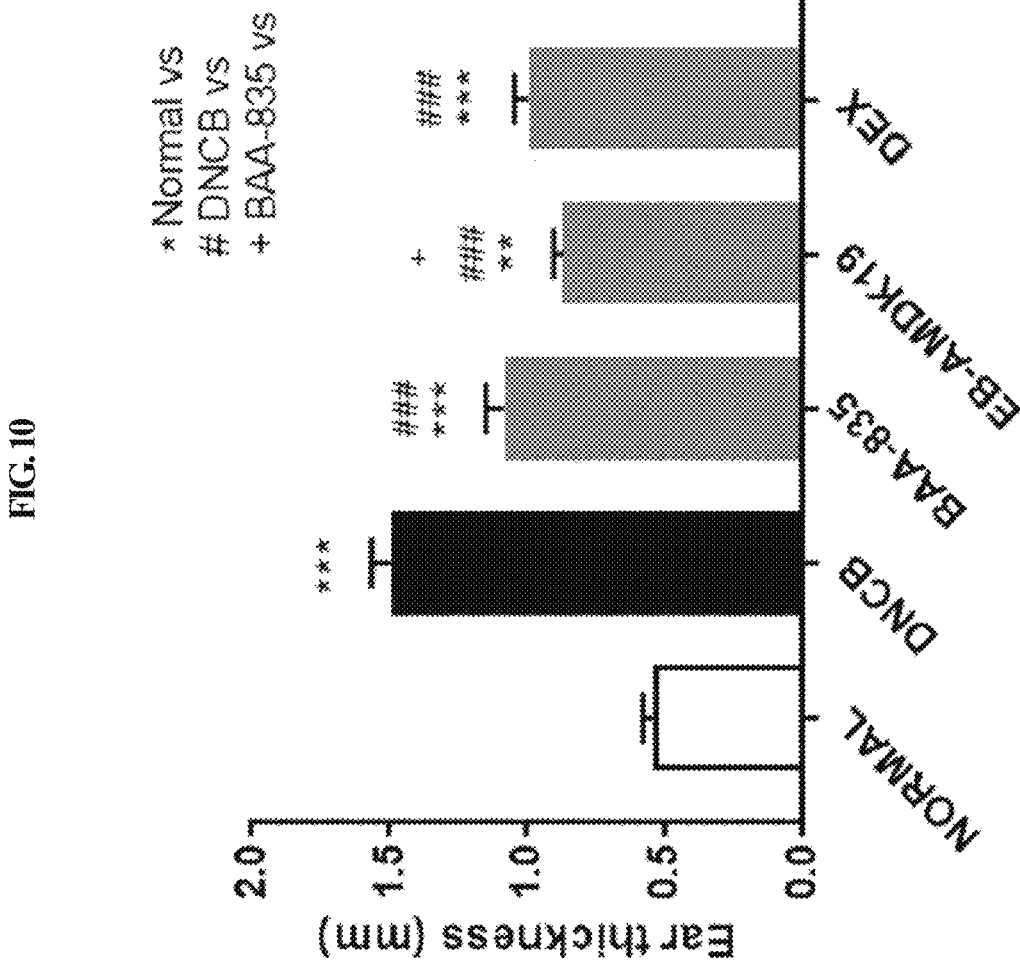
Figure 11:
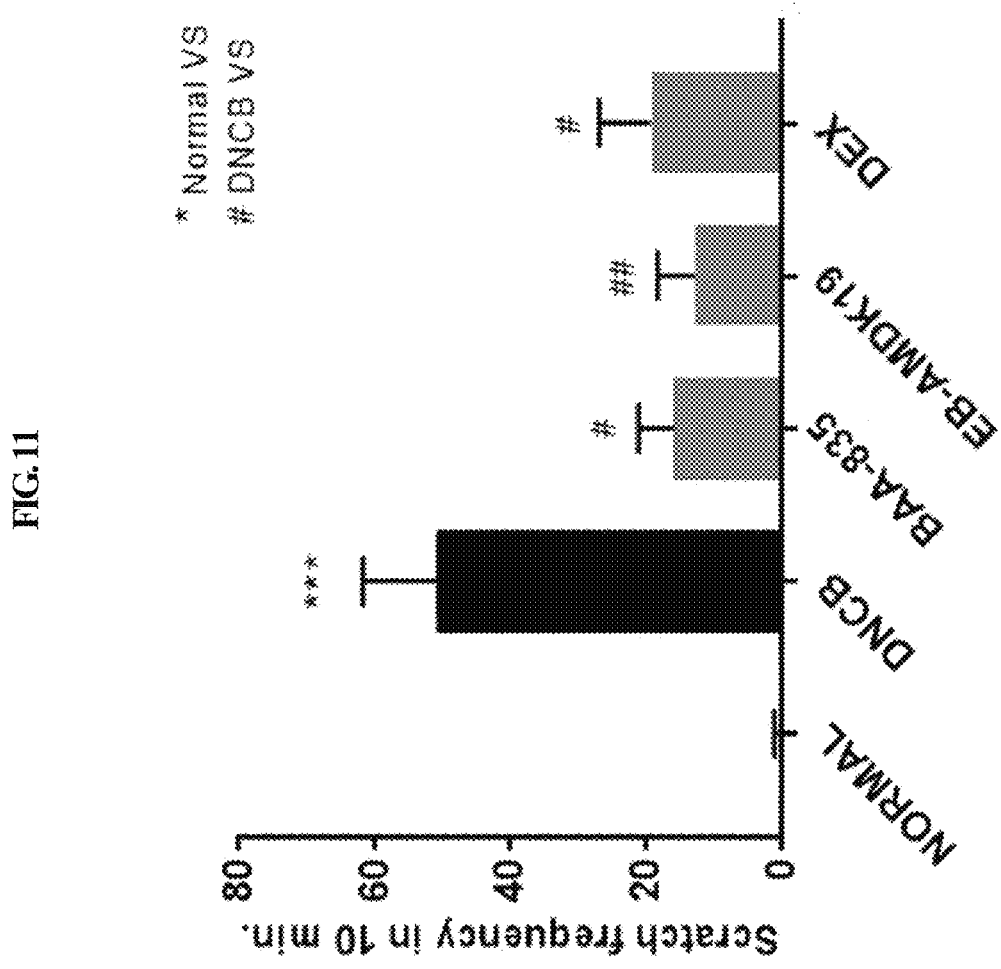
Figure 13:
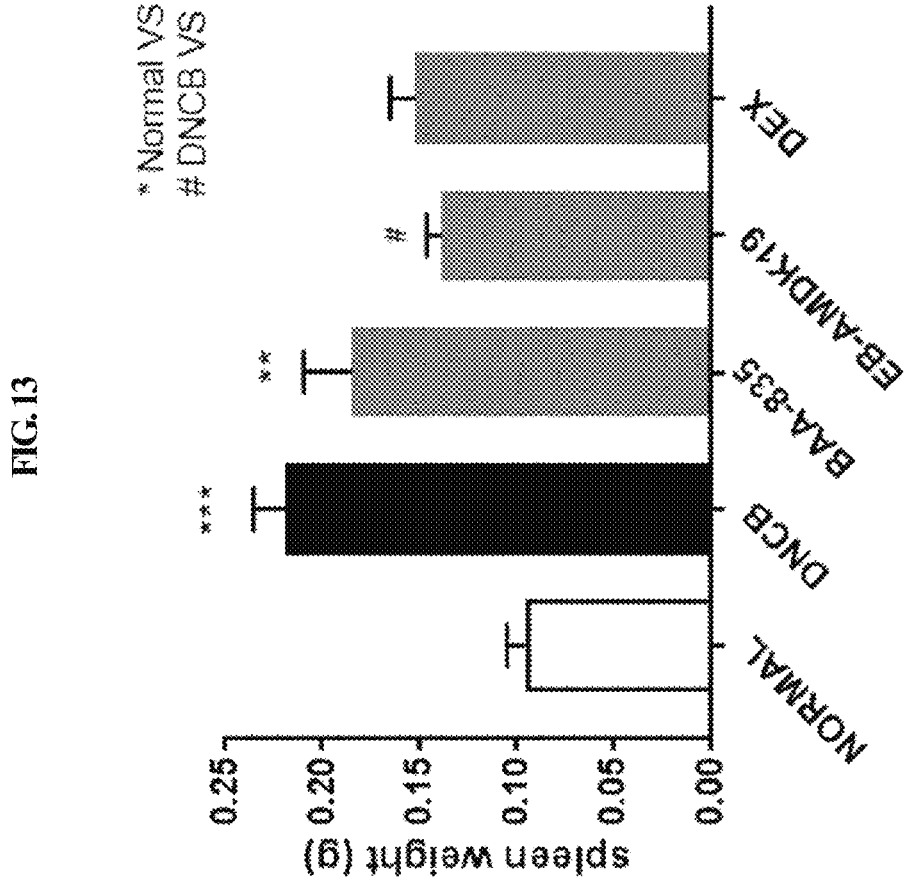
Figure 14:
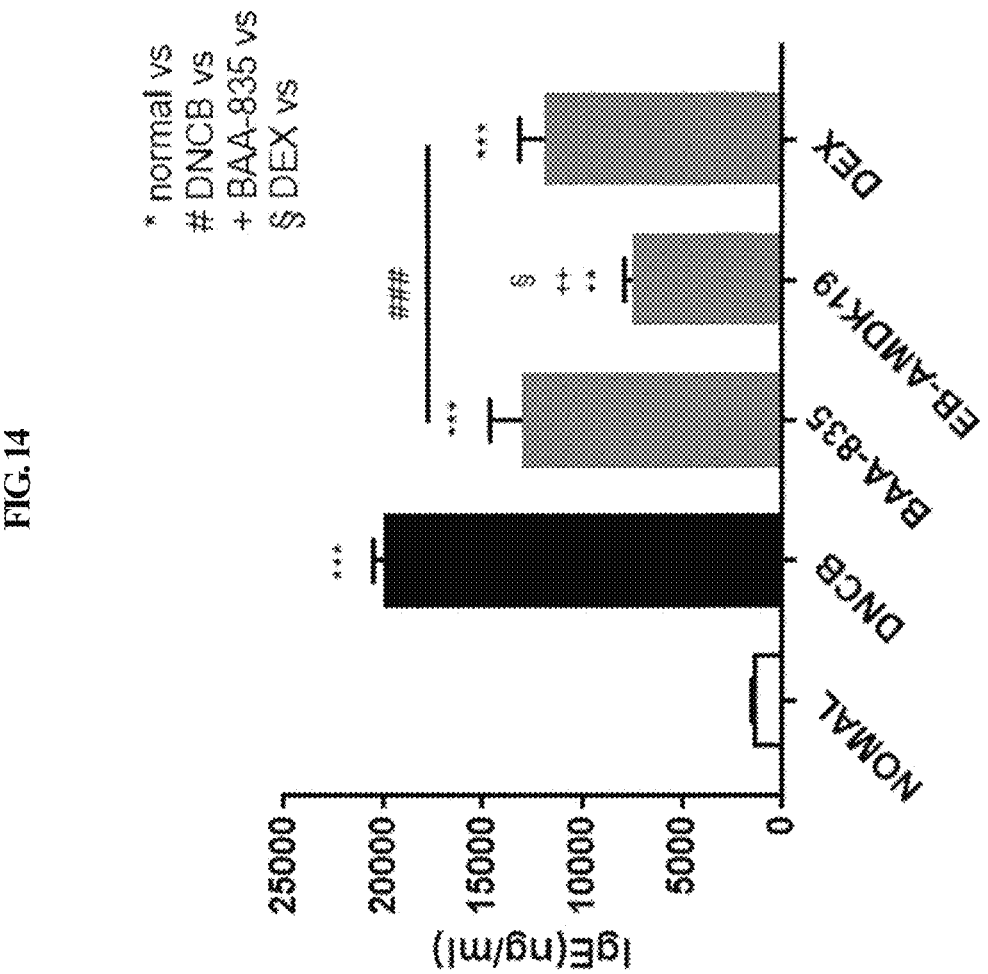
Figure 15A:
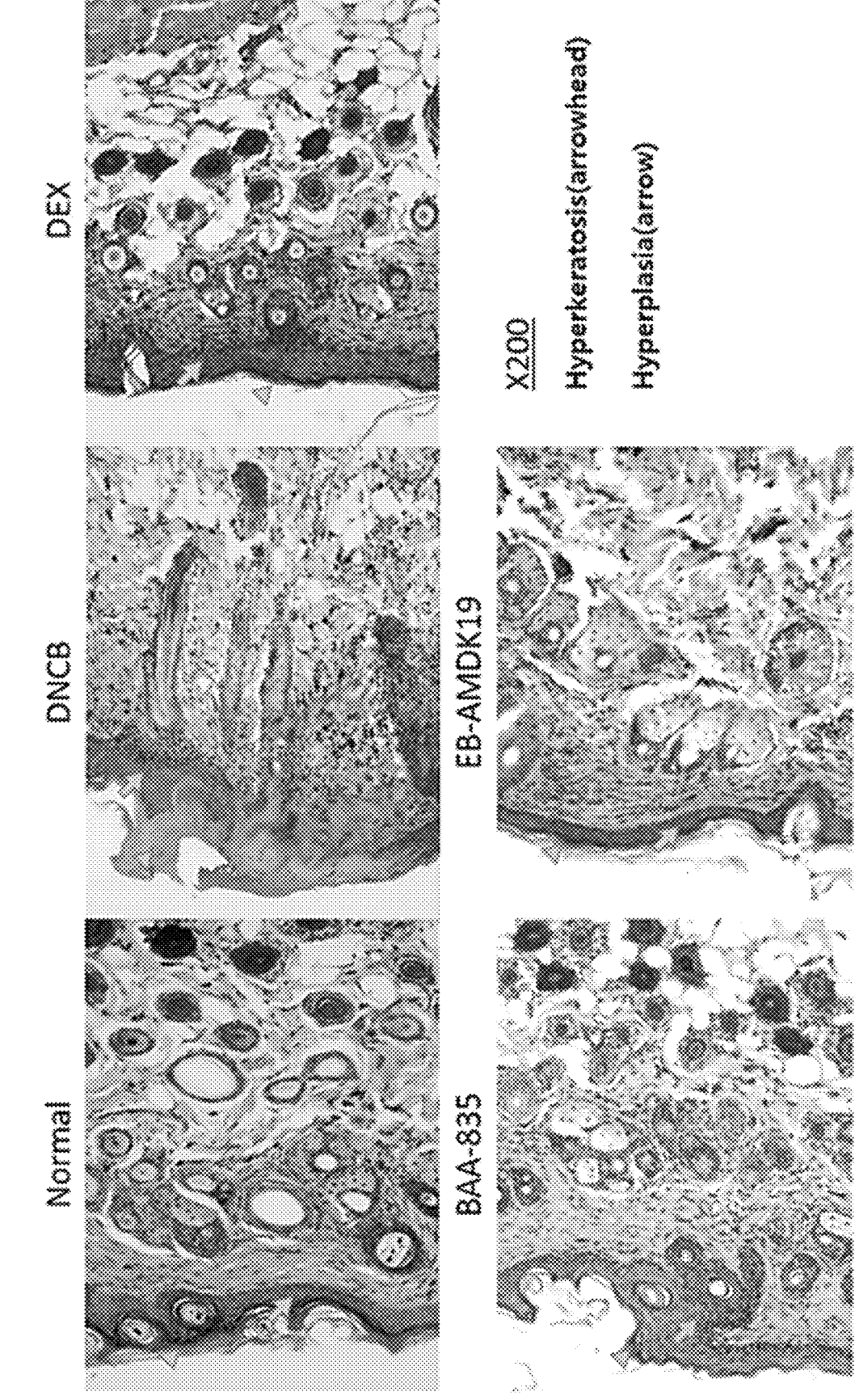
Figure 15B:
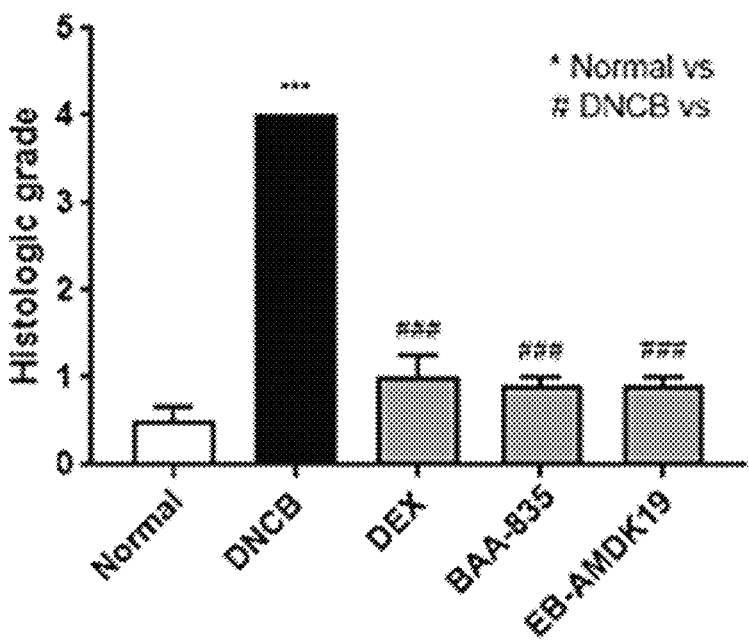
Figure 15C:
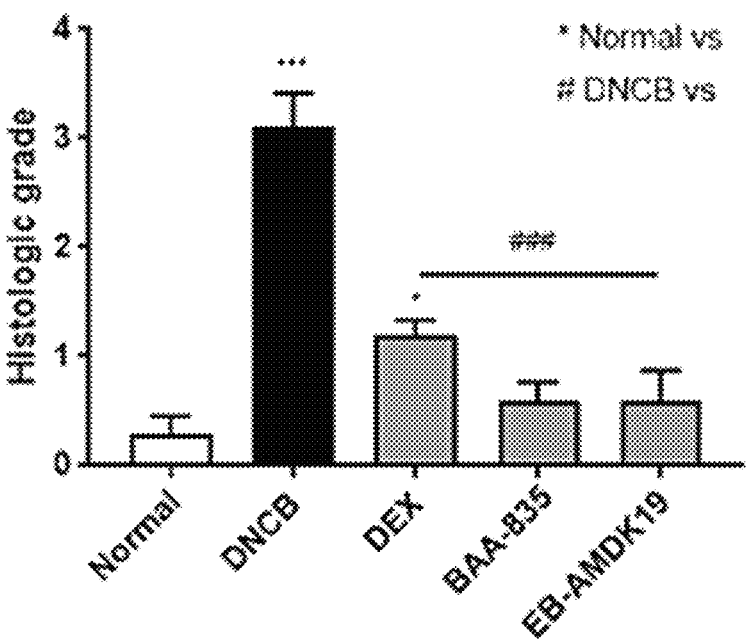
Figure 16:
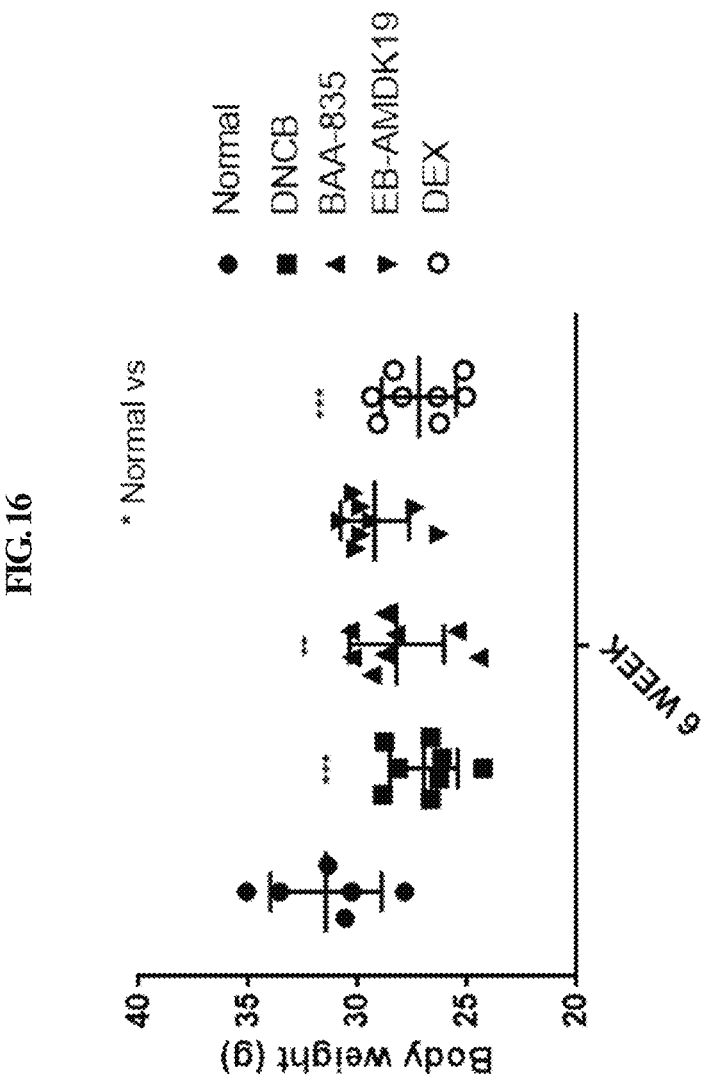
Figure 17B:
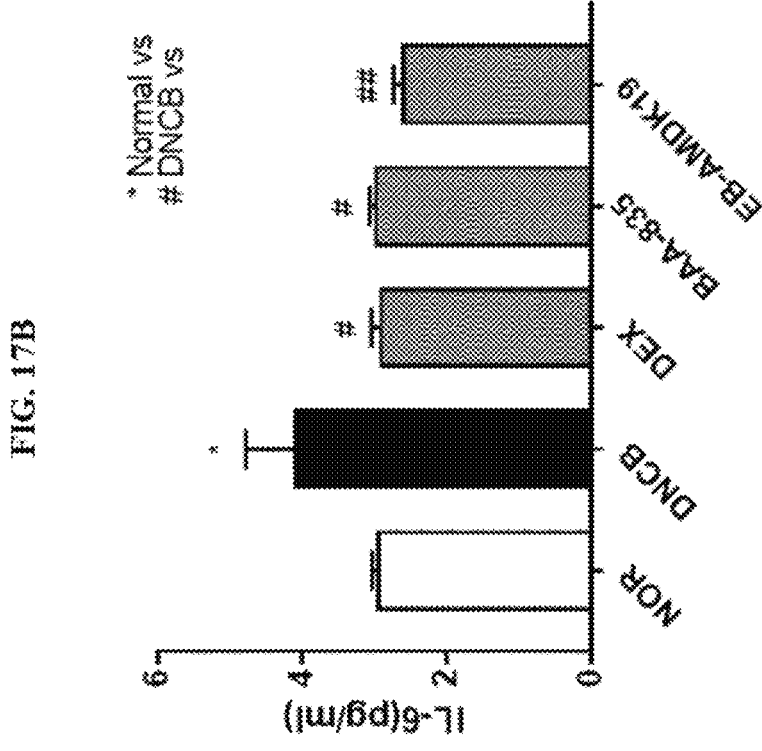
Figure 17A:
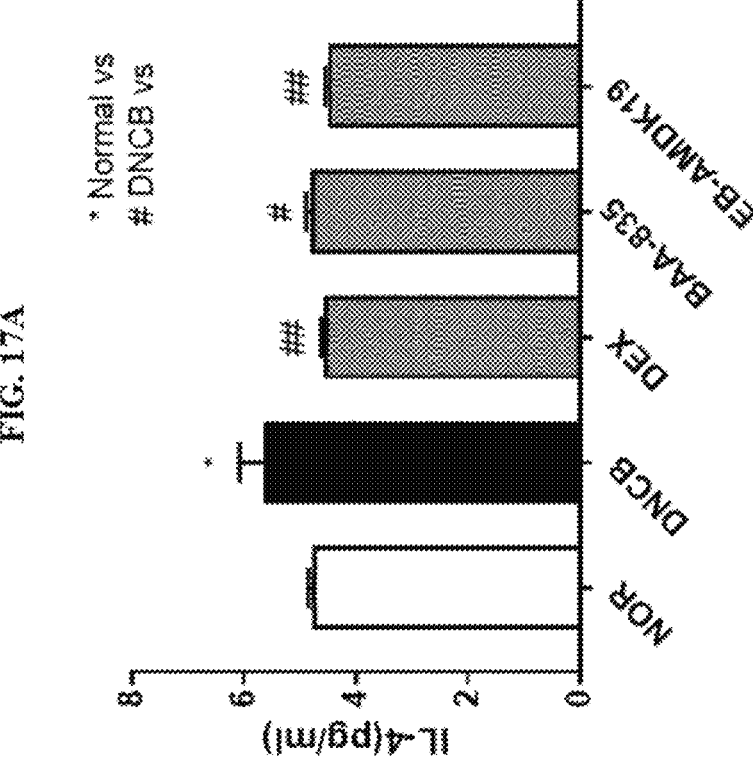
Figure 18B:
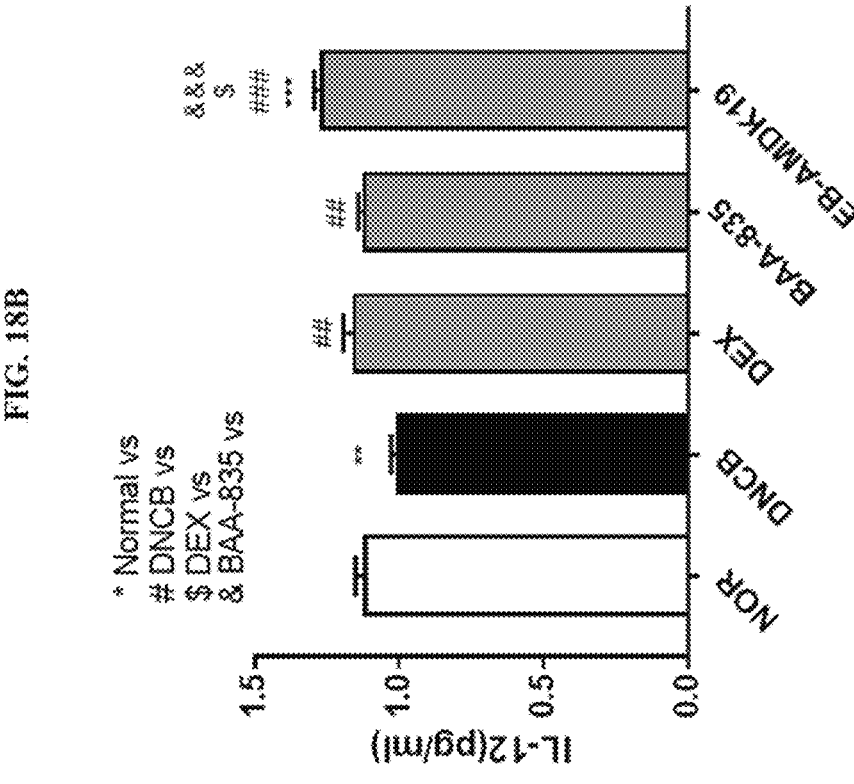
Figure 18A:
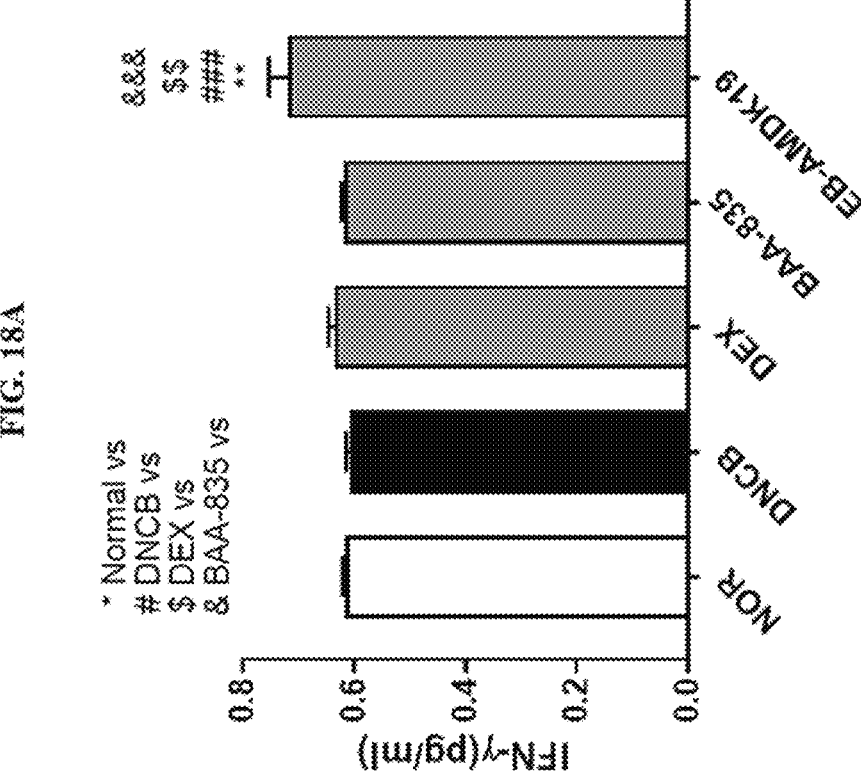

FIG. 6 shows the results of evaluating the *Akkermansia muciniphila* EB-AMDK19 strain of the present invention on the viability of colonic epithelial cells;

FIG. 7 depicts photographs showing the results of visually observing the pathological characteristics of the skin tissue of the mice of each experimental group in an example of the present invention;

FIG. 8 is a graph showing the change in dermatitis score caused by the *Akkermansia muciniphila* EB-AMDK19 strain of the present invention;

FIG. 9 depicts photographs showing a comparison of the degree of ear edema of mice between experimental groups in an example of the present invention;

FIG. 10 shows the results of analyzing changes in ear thicknesses in a group to which the *Akkermansia muciniphila* EB-AMDK19 strain of the present invention was administered, a positive control group (DEX), and a group to which the *Akkermansia muciniphila* ATCC BAA-835 strain was administered;

FIG. 11 is a graph showing the scratch frequency of experimental animals in the group to which the *Akkermansia muciniphila* EB-AMDK19 strain of the present invention was administered, a positive control group (DEX), and the group to which the *Akkermansia muciniphila* ATCC BAA-835 strain was administered;

Figure 12:
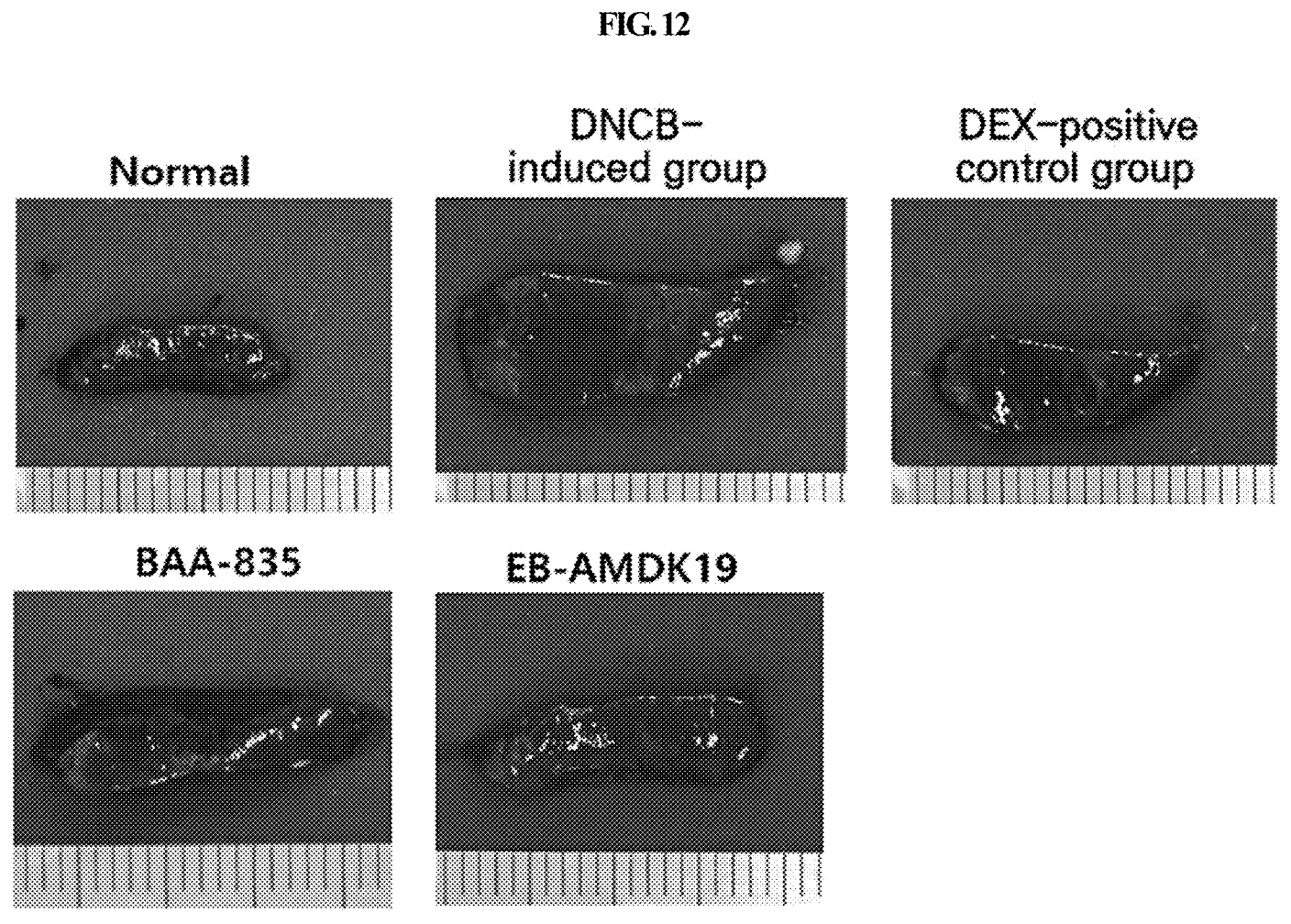

FIG. 12 depicts photographs of the spleens of a group to which the *Akkermansia muciniphila* EB-AMDK19 strain of the present invention was administered, a positive control group (DEX), and a group to which the *Akkermansia muciniphila* ATCC BAA-835 strain was administered;

FIG. 13 is a graph showing a composition of spleen weight between the group to which the *Akkermansia muciniphila* EB-AMDK19 strain of the present invention was administered, the positive control group (DEX), and the group to which the *Akkermansia muciniphila* ATCC BAA-835 strain was administered;

FIG. 14 is a graph showing changes in IgE, which is the most important immune marker that mediates allergic disease, in the group to which the *Akkermansia muciniphila* EB-AMDK19 strain of the present invention was administered, the positive control group (DEX), and the group to which the *Akkermansia muciniphila* ATCC BAA-835 strain was administered;

FIG. 15A, FIG. 15B, and FIG. 15C show the results of hematoxylin & eosin (H&E) staining of skin tissues collected from mice of each experimental group in an example of the present invention;

FIG. 16 shows the results of evaluating the effect of the *Akkermansia muciniphila* EB-AMDK19 strain of the present invention on the atopy-induced change in body weight after atopy induction;

FIG. 17A and FIG. 17B show the results of evaluating the effects of administration of the *Akkermansia muciniphila* EB-AMDK19 strain of the present invention on IL-4 and IL-6;

FIG. 18A and FIG. 18B show the results of evaluating the effects of administration of the *Akkermansia muciniphila* EB-AMDK19 strain of the present invention on blood Th1 cytokines IFN-γ and IL-12; and FIG. 19A, FIG. 19B, FIG. 20A, and FIG. 20B show the results of evaluating the effects of administration of the *Akkermansia muciniphila* EB-AMDK19 strain of the present invention on the production of blood Th1 cytokines and Th2 cytokines.

MODE FOR INVENTION

Hereinafter, the present invention will be described in more detail with reference to the accompanying drawings.

Unless otherwise defined, all technical and scientific terms used herein have the same meanings as commonly understood by those skilled in the art to which the present invention pertains.

As used herein, the term "about", when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Throughout the present specification, it is to be understood that when any part is referred to as "including" any component, it does not exclude other components, but may further include other components, unless otherwise specified.

As used herein, the term "atopic allergy" refers to a disease causing allergic reactions, and is meant to include asthma, atopic dermatitis, allergic rhinitis (hay fever), urticaria, anaphylaxis, angioedema, food allergy, etc.

As used herein, the team "preventing" refers to any action that suppresses or delays the onset of atopic disease by administration of the pharmaceutical composition according to the present invention.

As used herein, the terms "treat", "treating", or the like mean to alleviate symptoms, eliminate the causation of symptoms either on a temporary or permanent basis, or to prevent or slow the appearance of symptoms of the named disorder or condition.

As used herein, the term "ameliorating" refers to any action that reduces a parameter associated with an abnormal condition, for example, the severity of symptoms.

As used herein, the term "pharmaceutically acceptable" refers to compositions which are, within the scope of sound medical judgment, suitable for use in contact with the tissues of subjects (e.g., human beings) without excessive toxicity, irritation, allergic response, or other problem or complication, commensurate with a reasonable benefit/risk ratio.

Pharmabiotics are defined as bacterial cells of human origin, or their products, with a proven pharmacological role in health or disease ("Probiotics and phainabiotics," Bioeng Bugs. 2010 March-April; 1(2): 79-84.). One aspect of the present invention is directed to a pharmaceutical composition for preventing or treating atopic disease containing an *Akkermansia muciniphila* EB-AMDK19 strain (accession number: KCTC13761BP) as an active ingredient.

The *Akkermansia muciniphila* EB-AMDK19 strain (accession number: KCTC13761BP) of the present invention has the 16s rRNA gene of SEQ ID NO: 1.

The *Akkermansia muciniphila* EB-AMDK19 strain that is used in the present invention is a mucin-degrading bacterium isolated from the feces of healthy Koreans, is a monococcus or diplococcus with oval cells having a size of 0.5 to 1 μm, is anaerobic, is not motile, is gram-negative, and does not form endospores. The *Akkermansia muciniphila* EB-AMDK19 strain may use mucus as the sole source of carbon and nitrogen by producing several mucolytic enzymes, may metabolize various carbon sources, including glucose, galactose, N-acetylglucosamine and lactose, and produce, as major metabolites, short-chain fatty acids such as propionic acid and acetic acid.

IgE is a member of the immunoglobulin family that mediates allergic responses such as asthma, atopic dermatitis, rhinitis, anaphylaxis, and food allergies. IgE is secreted by, and expressed on the surface of B-cells or B-lymphocytes. IgE binds to B-cells through its Fc region to a low affinity IgE receptor, known as FcεRII, and also binds to monocytes, eosinophils and platelets. When a mammal is exposed to an allergen, B-cells bearing a surface-bound IgE antibody specific for the antigen are activated and developed into IgE-secreting plasma cells. In allergic conditions, production of IgE by B-cells induces secretion of histamine and other pro-inflammatory molecules and promotes the severity of disease.

Presence of elevated Immunoglobulin E (IgE) levels in serum is regarded as an integral part of the inflammatory cascade observed in allergic diseases such as asthma. Induction of allergen-specific IgE can be detected in animal models of allergic pulmonary inflammation as well as in human asthmatics and is an indication of the initiation of the relevant cellular (T and B cell axis) and humoral mechanisms that drive development of allergy. Hence, modulation of the allergen-specific IgE response by therapeutic intervention points to modulation of the mechanisms that fundamentally underpin development of allergy.

The pharmaceutical composition for preventing or treating atopic disease according to the present invention functions to achieve Th1/Th2 balance in a situation where Th2 is dominant. Therefore, the pharmaceutical composition is effective for preventing or treating atopic dermatitis, asthma, and rhinitis, which are caused by Th1/Th2 imbalance due to an excessive Th2 response. It is generally known that changes in cytokine levels in atopic dermatitis are caused by an immune system based on Th2 activation in which differentiation of undifferentiated T-helper cells 1 (Th1) to T-helper cells 2 (Th2) is highly promoted. In this Th2 cell activation process, Th2 cells produce IL-4, IL-5, IL-6, IL-13, IL-9 and IL-10.

In the present invention, the *Akkermansia muciniphila* EB-AMDK19 strains according to the invention are used as live bacteria or pasteurized bacteria. For use, the *Akkermansia muciniphila* EB-AMDK19 strain of the invention may be cultured, recovered by a separation process such as centrifugation, and dried, for example, freeze-dried to foam a probiotic. Pasteurization of the *Akkermansia muciniphila* EB-AMDK19 strain means heating the strain at a temperature of 50° C. to 100° C. for 10 minutes or more. For example, the strain may be pasteurized at 70° C. for 30 minutes.

The pharmaceutical composition of the present invention may contain, as an active ingredient, the *Akkermansia muciniphila* EB-AMDK19 strain in an amount of $10^8$ to $10^{12}$ CFU, or contain a culture product having the same CFU of live bacteria.

In one embodiment of the present invention, for use, the pharmaceutical composition containing the *Akkermansia muciniphila* EB-AMDK19 strain may be formulated in oral dosage forms, including powders, granules, tablets, capsules, suspensions, emulsions, syrup and aerosol, preparations for external application, suppositories, and sterile injectable solutions, according to respective conventional methods, but is not necessarily limited thereto.

The pharmaceutical composition of the present invention may be formulated as a product for intestinal or oral administration. In addition, the pharmaceutical composition of the present invention may be prepared in the form of enteric coated preparation in order for the composition to pass through the stomach and reach the small intestine safely and to release the active ingredient microorganism therein quickly, according to a known method.

In one embodiment of the present invention, liquid formulations for oral administration include suspensions, solutions, emulsions and syrup, and may contain, but are not necessarily limited to, various excipients, for example, wetting agents, sweetening agents, flavoring agents and preservatives, in addition to water and liquid paraffin, which are frequently used simple diluents.

In other embodiments, the pharmaceutical composition for preventing or treating atopic diseases according to the present invention may further contain at least one vitamin. The at least one vitamin may be fat-soluble or water-soluble vitamins. Suitable vitamins include, but are not necessarily limited to, vitamin D, vitamin C, vitamin A, vitamin E, vitamin B12, vitamin K, riboflavin, niacin, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

The pharmaceutical composition for preventing or treating atopic disease according to the present invention may further contain a known additional therapeutic agent having an effect of preventing and treating allergic disease or atopic dermatitis. Additional therapeutic agents that may be used in the present invention are immunosuppressants, analgesics, steroids, non-steroidal anti-inflammatory agents (NSAIDs) or cytokine antagonists, and combinations thereof. Examples of the immunosuppressants include, but are not necessarily limited to, calcineurin inhibitors including glucocorticoid, cyclosporine, tacrolimus (FK506), pimecrolimus and ISA(TX)247, rapamycin, a Type IV PDE inhibitor, mycophenolate mofetil, dexamethasone, and the like. For example, all kinds of known immunosuppressants may be used herein. In addition, one immunosuppressant may be used alone, or two or more immunosuppressants may be used in combination. Preferably, at least one selected from the group consisting of cyclosporine, tacrolimus, dexamethasone, and pimecrolimus may be used as the immunosuppressant. Where the pharmaceutical composition according to the present invention is used in combination with a second therapeutic agent, it may be administered sequentially or simultaneously with the second therapeutic agent, and may be administered alone or several times.

The pharmaceutical composition of the present invention may further contain a pharmaceutically acceptable carrier and/or excipient in addition to the active ingredient, and may be formulated with various additives which are commonly in the pharmaceutical field, such as binders, disintegrants, coating agents, and lubricants.

Excipients that may be used in the present invention include saccharides such as sucrose, lactose, mannitol and glucose, and starches such as corn starch, potato starch, rice starch, and partially pregelatinized starch. Binders include polysaccharides such as dextrin, sodium alginate, carrageenan, guar gum, acacia gum and agar; naturally-occurring macromolecular substances such as tragacanth, gelatin, and gluten; cellulose derivatives such as hydroxypropylcellulose, methylcellulose, hydroxypropylmethyl cellulose, ethylcellulose, hydroxypropylethylcellulose, and carboxymethylcellulose sodium; and polymers such as polyvinylpyrrolidone, polyvinyl alcohol, polyvinyl acetate, polyethylene glycol, polyacrylic acid, polymethacrylic acid, and vinyl acetate resin.

Examples of disintegrants that may be used in the present invention include cellulose derivatives such as carboxymethylcellulose, calcium carboxymethylcellulose, and low-substituted hydroxypropylcellulose; and starches such as sodium carboxymethyl starch, hydroxypropyl starch, corn starch, potato starch, rice starch, and partially pregelatinized starch.

Examples of lubricants that may be usable in the present invention include talc, stearic acid, calcium stearate, magnesium stearate, colloidal silica, hydrous silicon dioxide, and various types of waxes and hydrogenated oils.

Coating agents include, but are not necessarily limited to, water-insoluble polymers such as dimethylaminoethyl methacrylate-methacrylic acid copolymers, polyvinylacetaldiethylaminoacetate, ethylacrylate-methacrylic acid copolymers, ethylacrylate-methylmethacrylate-chlorotrimethyl ammonium ethylmethacrylate copolymers, and ethylcellulose; enteric polymers such as methacrylic acid-ethyl acrylate copolymers, hydroxypropylmethyl cellulose phthalate, and hydroxypropylmethyl cellulose acetate succinate; and water-soluble polymers such as methylcellulose, hydroxypropylmethylcellulose, polyvinylpyrrolidone, and polyethylene glycol.

The dosage of the strain as an active ingredient in the pharmaceutical composition for preventing or treating atopic disease according to the present invention may be determined depending on factors, including various types of diseases, the patients' age, body weight, sex and medical condition, severity of the condition, sensitivity to a drug, the time of administration, the route of administration, the rate of excretion, the duration of treatment, and drugs used in combination with the composition, as well as other factors well known in the medical field. Thus, the dosage regimen may vary widely, but it is important to administer a minimal amount that can achieve the maximum effect without side effects taking into consideration all of the above factors, and this dosage regimen may be determined routinely by a person skilled in the art using standard methods.

Generally, for adults, $1\times10^8$ or more live or pasteurized bacteria, preferably $1\times10^8$ to $1\times10^{12}$ live or pasteurized bacteria, may be taken once or several times as needed. In one embodiment of the present invention, the content of the *Akkermansia muciniphila* EB-AMDK19 strain in the pharmaceutical composition for preventing or treating atopic disease is not particularly limited as long as the pharmaceutical composition contains the strain. However, the pharmaceutical composition may contain the *Akkermansia muciniphila* EB-AMDK19 strain at a concentration of $1\times10^8$ cells/ml to $1\times10^{10}$ cells/ml, but the concentration is not necessarily limited thereto. For example, the concentration of the *Akkermansia muciniphila* EB-AMDK19 strain in the pharmaceutical composition may be $1\times10^8$ cells/ml to $1\times10^{10}$ cells/ml, $2\times10^8$ cells/ml to $1\times10^{10}$ cells/ml, $3\times10^8$ cells/ml to $1\times10^{10}$ cells/ml, $5\times10^8$ cells/ml to $1\times10^{10}$ cells/ml, $1\times10^8$ cells/ml to $5\times10^9$ cells/ml, $2\times10^8$ cells/ml to $5\times10^9$ cells/ml, $3\times10^8$ cells/ml to $5\times10^9$ cells/ml, or $5\times10^8$ cells/ml to $5\times10^9$ cells/ml, but is not necessarily limited thereto.

Another aspect of the present invention is directed to a food or health functional food containing the *Akkermansia muciniphila* EB-AMDK19 strain or a culture or dried product thereof.

The food containing the strain according to the present invention may be taken as various foods or nutritional products such as milk or dairy products, or taken as food supplements or health functional foods. According to one embodiment of the present invention, examples of the products include, but are not necessarily limited to, foods such as dairy products, beverages, juices, soups, or children's foods.

Still another aspect of the present invention is directed to a cosmetic composition for alleviating or ameliorating atopic dermatitis containing the *Akkermansia muciniphila* EB-AMDK19 strain or a culture or dried product thereof. The cosmetic composition of the present invention may contain ingredients that are commonly used in cosmetic compositions, in addition to the above active ingredient, and may contain conventional adjuvants such as antioxidants, stabilizers, solubilizers, vitamins, colorants and flavoring agents, and carriers.

The cosmetic composition may be characterized by having a function of ameliorating one or more skin conditions selected from the group consisting of skin allergies, skin urticaria, atopic dermatitis, psoriasis, fungal infections, and eczema, but the function is not necessarily limited to amelioration of these skin conditions.

The cosmetic composition of the present invention may be formulated in any conventional form known in the art. For example, the cosmetic composition may be formulated in the form of solution, suspension, emulsion, paste, gel, cream, lotion, powder, soap, surfactant-containing cleansing, oil, powder foundation, emulsion foundation, wax foundation, pack, mask pack, massage cream, and spray. More specifically, the cosmetic composition may be formulated in the form of skin softener, lotion, nourishing cream, massage cream, essence, eye cream, cleansing cream, cleansing foam, cleansing water, spray or powder.

Hereinafter, the present invention will be described with reference to examples. It is to be understood, however, that the following examples serve merely to illustrate the present invention, and the scope of the present invention is not limited by the following examples

EXAMPLES

Examples 1: Isolation and Identification of *Akkermansia muciniphila* Strain 1.1. Isolation and Identification of Strain To isolate *Akkermansia muciniphila* from the feces of a healthy Korean (female, 35 years old, BMI 23.3), a strain was isolated after selective culture using mucin medium (0.4 g $KH_2PO_4$; 0.53 g $Na_2HPO_4$; 0.3 g NaCl; 0.1 g $MgCl_2$ $6(H_2O)$; 0.11 g $CaCl_2$ 0.4 g/L, 1 ml acid trace element solution, 1 ml alkaline trace element solution, 1 ml vitamin solution, 2.5 g/L porcine gastric mucus (type III)), and 0.25 g/L sodium sulfide nonahydrate) according to the method of Derrien (Derrien et al., 2004).

Figure 1:
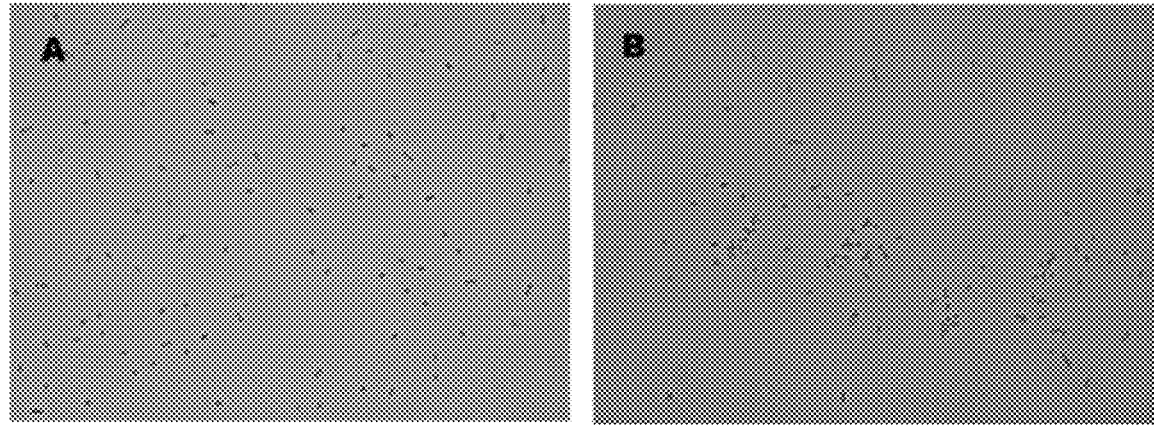
FIG. 1 shows the results of microscopic observation of the *Akkermansia muciniphila* EB-AMDK19 strain of the present invention and an *Akkermansia muciniphila* ATCC BAA-835 strain which is a type strain.
Figure 2:
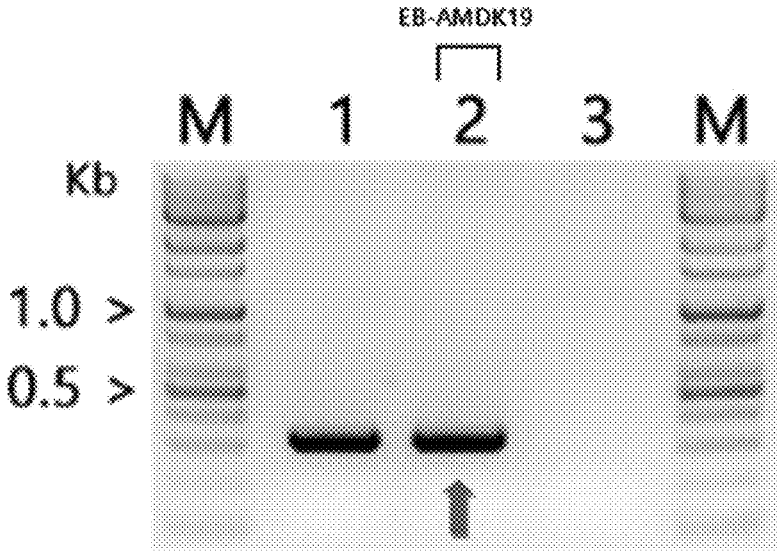
FIG. 2 shows the results of PCR analysis of the *Akkermansia muciniphila* EB-AMDK19 strain of the present invention and the *Akkermansia muciniphila* ATCC BAA-835 strain.

In order to confirm whether the isolated strain was an *Akkermansia muciniphila* strain, the isolated strain was observed under a microscope, and the results are shown in FIG. 1. In addition, PCR analysis was performed using the AM-specific primers shown in Table 1 below, and the results are shown in FIG. 2.

In FIG. 1, A is a micrograph of an *Akkermansia muciniphila* ATCC BAA-835 strain, and B is a micrograph of the *Akkermansia muciniphila* ATCC BAA-835 strain at 1,000× magnification. In FIG. 2, lane M is a DNA size marker, lane 1 represents a positive control (ATCC BAA-835), lane 2 represents the *Akkermansia muciniphila* EB-AMDK19 strain, and lane 3 represents a negative control (distilled water). As a result, as shown in FIG. 2, it could be confirmed that the strain of the present invention showed a band similar to that of the positive control *Akkermansia muciniphila* ATCC BAA-835 strain.

TABLE 1

| Desig-nation | Direction | Sequence (5'→3') | Amplicon size | SEQ ID NO |
|---|---|---|---|---|
| AM1 | Forward | CAG CAC GTG AAG GTG GGG AC | 327 bp | SEQ ID NO: 2 |

TABLE 1-continued

| Desig-nation | Direction | Sequence (5'→3') | Amplicon size | SEQ ID NO |
|---|---|---|---|---|
| AM2 | Reverse | CCT TGC GGT TGG CTT CAG AT | | SEQ ID NO: 3 |

1.2. Examination of Carbohydrate Utilization of Isolated *Akkermansia muciniphila* Strain In order to examine the sugar utilization of the *Akkermansia muciniphila* EB-AMDK19 strain of the present invention isolated as described above, the strain was cultured using the API50CH kit (Biomerieux, France), and whether the strain would utilize each carbohydrate was compared with that of the type strain (ATCC BAA-835). The results are shown in Table 2 below.

TABLE 2

| No | Carbohydrates | ATCC BAA-835 | EB-AMDK19 |
|---|---|---|---|
| 0 | Negative control | – | – |
| 1 | Glycerol | – | – |
| 2 | Erythritol | – | – |
| 3 | D-Arabinose | w | w |
| 4 | L-Arabinose | w | w |
| 5 | Ribose | + | w |
| 6 | D-Xylose | w | w |
| 7 | L-Xylose | w | w |
| 8 | Adonitol | – | – |
| 9 | β-Methyl-xyloside | – | – |
| 10 | D-Galactose | w | + |
| 11 | D-Glucose + Mucin | + | + |
| 12 | D-Fructose | w | – |
| 13 | D-Mannose | + | w |
| 14 | L-Sorbose | – | – |
| 15 | L-Rhamnose | – | – |
| 16 | Dulcitol | – | – |
| 17 | Inositol | – | – |
| 18 | D-Mannitol | – | – |
| 19 | D-Sorbitol | – | – |
| 20 | Methyl-α D-mannopyranoside | – | – |
| 21 | Methyl-α D-glucopyranoside | – | – |
| 22 | N-Acetylglucosamine | + | + |
| 23 | Amygdaline | – | – |
| 24 | Arbutine | – | – |
| 25 | Esculine | – | – |
| 26 | Salicine | – | – |
| 27 | D-Cellobiose | – | – |
| 28 | D-Maltose | – | – |
| 29 | D-Lactose (bovine origin) | + | + |
| 30 | D-Melibiose | – | – |
| 31 | D-Saccharose (sucrose) | – | – |
| 32 | D-Trehalose | – | – |
| 33 | Inuline | – | – |
| 34 | D-Melezitose | – | – |
| 35 | D-Raffinose | – | – |
| 36 | Amidon (starch) | – | – |
| 37 | Glycogene | – | – |
| 38 | Xylitol | – | – |
| 39 | Gentiobiose | – | – |
| 40 | D-Turanose | – | – |
| 41 | D-Lyxose | w | w |
| 42 | D-Tagatose | – | – |
| 43 | D-Fucose | – | – |
| 44 | L-Fucose | + | + |
| 45 | D-Arabitol | – | – |
| 46 | L-Arabitol | – | – |
| 47 | Potassium Gluconate | – | – |

TABLE 2-continued

| No | Carbohydrates | ATCC BAA-835 | EB-AMDK19 |
|---|---|---|---|
| 48 | Potassium 2-Ketogluconate | – | – |
| 49 | Potassium 5-Ketogluconate Ketogluconate | w | w |

+: growth,
w: weak growth,
–: no growth,

As can be seen in Table 2 above, it was confirmed that the *Akkermansia muciniphila* EB-AMDK19 strain of the present invention was different in the utilization of ribose, D-galactose, D-fructose and D-mannose from the type strain *Akkermansia muciniphila* ATCC BAA-835 strain.

1.3. Whole Genome Sequencing

In order to analyze the variation between the isolated *Akkermansia muciniphila* EB-AMDK19 strain and the *Akkermansia muciniphila* ATCC BAA-835 strain at the genome level, the whole genome sequence of the isolated strain was analyzed using the PacBio technique and compared with that of the type strain the *Akkermansia muciniphila* ATCC BAA-835 strain (Tables 3 and 4).

TABLE 3

| Genome statistics | Strain | |
|---|---|---|
| | ATCC BAA-835 | EB-AMDK19 |
| Accession no. | CP001071 | CP025834 |
| Assembly level | Complete | Complete |
| Seq. category | Chromosome | Chromosome |
| Total size (Mb) | 2.6641 | 2.7242 |
| GC (%) | 55.8 | 55.3 |
| Protein | 2,246 | 2,140 |
| Gene | 2,321 | 2,357 |
| CDS | 2,257 | 2,293 |
| Coding | 2,246 | 2,250 |
| rRNA | 9 | 9 |
| tRNA | 52 | 52 |
| Other RNA | 3 | 3 |
| Pseudogene | 11 | 44 |
| Symmetrical identity (%) | — | 90.1368 |

*Symmetrical identity is similarity to ATCC BAA-835

TABLE 4

| | Gene | Strain | |
|---|---|---|---|
| | | ATCC BAA-835 | EB-AMDK19 |
| Amuc_1098 | Sequence length | 901 | 900 |
| | Align identity (%) | 100 | 99.3 |
| | Mismatch no. | 0 | 5 |
| | Insertion no. | 0 | 0 |
| | Deletion no. | 0 | 1 |
| Amuc_1099 | Sequence length | 337 | 337 |
| | Align identity (%) | 100 | 100 |
| | Mismatch no. | 0 | 0 |
| | Insertion no. | 0 | 0 |
| | Deletion no. | 0 | 0 |
| Amuc_1100 | Sequence length | 316 | 316 |
| | Align identity (%) | 100 | 99.4 |
| | Mismatch no. | 0 | 2 |
| | Insertion no. | 0 | 0 |
| | Deletion no. | 0 | 0 |
| Amuc_1101 | Sequence length | 612 | 612 |
| | Align identity (%) | 100 | 99.2 |
| | Mismatch no. | 0 | 5 |

TABLE 4-continued

| | Gene | Strain | |
|---|---|---|---|
| | | ATCC BAA-835 | EB-AMDK19 |
| | Insertion no. | 0 | 0 |
| | Deletion no. | 0 | 0 |
| Amuc_1102 | Sequence length | 237 | 237 |
| | Align identity (%) | 100 | 98.7 |
| | Mismatch no. | 0 | 3 |
| | Insertion no. | 0 | 0 |
| | Deletion no. | 0 | 0 |
| Gene_cluster | Sequence length | 2403 | 2402 |
| | Align identity (%) | 100 | 99.3 |
| | Mismatch no. | 0 | 15 |
| | Insertion no. | 0 | 0 |
| | Deletion no. | 0 | 1 |

* For Gene_cluster, the length of 5 genes

As can be seen in Tables 3 and 4 above, the whole genome sequencing data of the *Akkermansia muciniphila* EB-AMDK19 strain did differ from those of the type strain *Akkermansia muciniphila* ATCC BAA-835 strain.

1.4. Random Amplified Polymorphic DNA (RAPD) Analysis

In order to verify whether the *Akkermansia muciniphila* EB-AMDK19 strain isolated as described above would be the same as the previously reported type strain *Akkermansia muciniphila* ATCC BAA-835 strain of the same species, RAPD analysis, a kind of molecular typing, was performed. To this end, the genomic DNA extracted from the isolated strain was amplified using the universal primers shown in Table 5 below, and then electrophoresed on 1% agarose gel for 1 hour and 30 minutes, and the DNA fragment patterns were compared on a UV transilluminator. The results are shown in FIG. 3.

TABLE 5

| Designation | Direction | Sequence (5'→3') | SEQ ID NO |
|---|---|---|---|
| ERIC-1 | Forward | ATG TAA GCT CCT GGG GAT TCA C | SEQ ID NO: 4 |
| ERIC-2 | Reverse | AAG TAA GTG ACT GGG GTG AGC G | SEQ ID NO: 5 |
| (GTG)$_5$ | Forward/ Reverse | GTG GTG GTG GTG GTG | SEQ ID NO: 6 |

Figure 3:
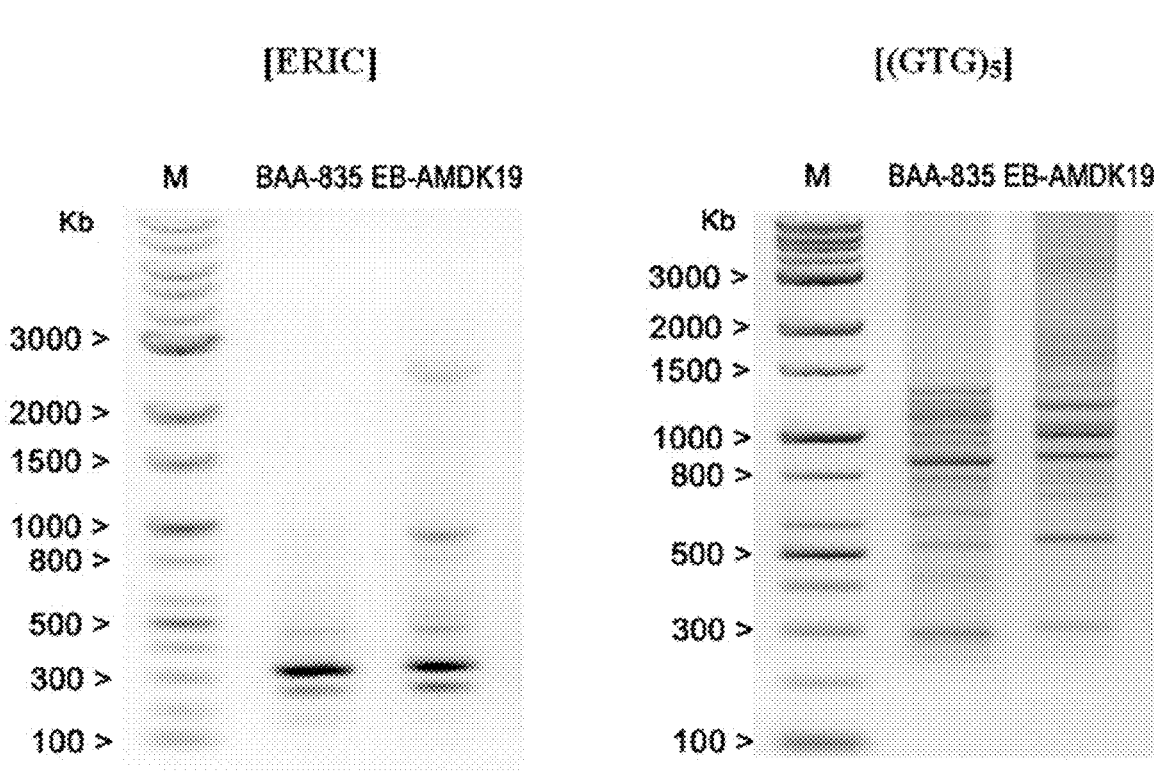
FIG. 3 shows the results of RAPD (Random Amplified Polymorphic DNA) analysis of the genomic DNAs of the present invention and the *Akkermansia muciniphila* ATCC BAA-835 strain.

As can be seen in FIG. 3, the *Akkermansia muciniphila* EB-AMDK19 strain of the present invention showed a RAPD band pattern different from that of the type strain *Akkermansia muciniphila* ATCC BAA-835. Thus, it was confirmed that the *Akkermansia muciniphila* EB-AMDK19 strain of the present invention was a strain different from the type strain *Akkermansia muciniphila* ATCC BAA-835, even though it was of the same species of the type strain *Akkermansia muciniphila* ATCC BAA-835.

1.5. Phylogenetic Tree Analysis of Full-Length 16S rRNA Gene Sequences

For full-length 16S rRNA gene sequencing of the *Akkermansia muciniphila* EB-AMDK19 strain isolated as described above, the 16S rRNA gene was amplified using the 27F and 1541R primers shown in Table 6 below, and then sequencing thereof was performed using the 3730×1 DNA analyzer. A phylogenetic tree was prepared using the EB-AMDK19 gene sequence obtained as described above and already published 16S rRNA gene sequences of other strains of the same species, and is shown in FIG. 4.

TABLE 6

| Desig-nation | Direction | Sequence (5'→3') | Amplicon size | SEQ ID NO |
|---|---|---|---|---|
| 27F | Forward | AGA GTT TGA TCM TGG CTC AG | 1,505 bp | SEQ ID NO: 7 |
| 1541R | Reverse | AAG GAG GTG ATC CAG CCG CA | | SEQ ID NO: 8 |

Figure 4:
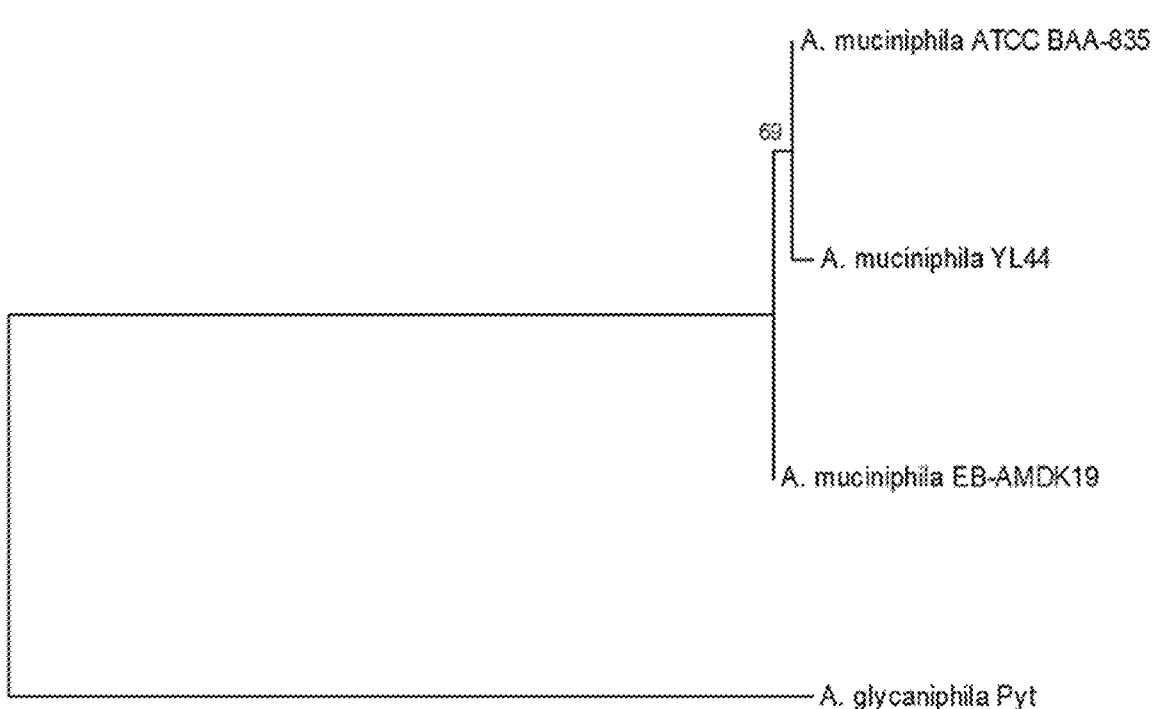
FIG. 4 shows the phylogenetic relationship between the *Akkermansia muciniphila* EB-AMDK19 strain of the present invention and other *Akkermansia muciniphila* strains.

As shown in FIG. 4, as a result of analyzing the evolutionary relationship between the strains through the phylogenetic tree analysis following the 16s rRNA gene sequencing, it was confirmed that the *Akkermansia muciniphila* EB-AMDK19 strain was a strain belonging to the *Akkermansia muciniphila* species in genetics terms. The *Akkermansia muciniphila* EB-AMDK19 strain isolated from the human feces was identified by a biochemical method (API) and a molecular biological method (16s rRNA sequencing, RAPD, and full-length screening) using *Akkermansia muciniphila*$^T$ (ATCC BAA-835) as a control, and it was confirmed through an antibiotic resistance test described below that the *Akkermansia muciniphila* EB-AMDK19 strain is a safe strain capable of having the function of probiotics. Based on these results, the isolated *Akkermansia muciniphila* strain was named "*Akkermansia muciniphila* EB-AMDK19" strain, and was deposited with the Korean Collection for Type Culture (KCTC), the Korea Research Institute of Bioscience and Biotechnology, under accession number KCTC13761BP.

Example 2: Safety Test for *Akkermansia muciniphila* EB-ANDK19 Strain

2.1. Antibiotic Resistance

In order to examine the antibiotic sensitivity of the *Akkermansia muciniphila* EB-AMDK19 strain isolated as described above, the minimum inhibitory concentrations (MICs) of piperacillin-tazobactam (PTZ), ceftizoxime (CTZ), chloramphenicol (CHL), clindamycin (CLI), meropenem (MEM), moxifloxacin (MXF), metronidazole (MTZ), and ciprofloxacin (CIP), which are antibiotics for anaerobic bacteria, were determined according to the broth microdilution method of the Clinical & Laboratory Standard Institute (CLSI) guideline (CLSI, 2017), and the results are shown in Table 7 below.

TABLE 7

| | MIC$^a$ Breakpoints (µg/ml) | | | QC ATCC 29741$^b$ | Test strains ATCC BAA-835 | EB-AMDK19 |
|---|---|---|---|---|---|---|
| Antibiotic | S | I | R | | | |
| PTZ | ≤32/4 | 64/4 | 128/4 | 8/4 | ≤0.5/4 (S) | ≤0.5/4 (S) |
| CTZ | ≤32 | 64 | ≥128 | 16 | 2 (S) | 1 (S) |
| CHL | ≤8 | 16 | ≥32 | 8 | 4 (S) | 4 (S) |
| CLI | ≤2 | 4 | ≥8 | 4 | ≤0.125 (S) | 4 (I) |
| MEM | ≤4 | 8 | ≥16 | 0.5 | 1 (S) | 0.5 (S) |
| MXF | ≤2 | 4 | ≥8 | 8 | >32 (R) | >32 (R) |

TABLE 7-continued

| | MIC$^a$ Breakpoints (µg/ml) | | | QC ATCC 29741$^b$ | Test strains ATCC BAA-835 | EB-AMDK19 |
|---|---|---|---|---|---|---|
| Antibiotic | S | I | R | | | |
| MTZ | ≤8 | 16 | ≥32 | 2 | ≤0.25 (S) | 0.5 (S) |
| CIP | ≤1 | 2 | ≥4 | >32 | >32 (R) | 32 (R) |

PTZ: Piperacillin-tazobactam,
CTZ: ceftizoxime (3$^{rd}$ gen),
CHL: chloramphenicol,
CLI: clindamycin,
MEM: meropenem,
MXF: moxifloxacin (4$^{th}$ gen),
MTZ: metronidazole,
CIP: ciprofloxacin (2$^{nd}$ gen),
$^a$MIC: minimal inhibitory concentration,
$^b$*Bacteroides thetiotaomicron* ATCC 29741

As can be seen in Table 7 above, the *Akkermansia muciniphila* EB-AMDK19 strain of the present invention exhibited moderate resistance to clindamycin, and exhibited resistance to moxiproxacin and ciprofloxacin, which are fluoroquinolone-based antibiotics, and showed sensitivity to all the other antibiotics. The antibiotic resistance pattern of the *Akkermansia muciniphila* EB-AMDK19 strain was slightly different from that of the type strain *Akkermansia muciniphila* ATCC BAA-835 strain. It can be confirmed that the *Akkermansia muciniphila* EB-AMDK19 strain according to the present invention is a safe strain having no resistance to most antibiotics.

2.2. Analysis of Hemolytic Activity and Cytotoxicity

Figure 5:
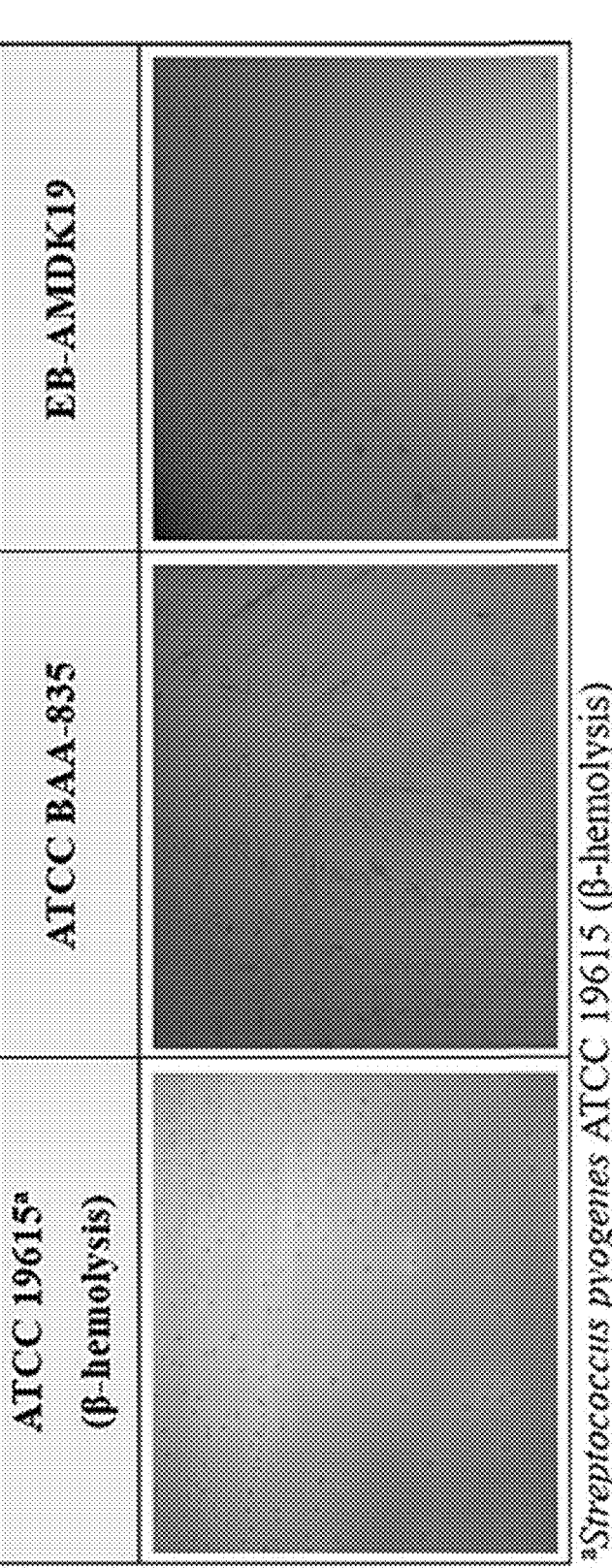
FIG. 5 shows the results of a hemolytic activity test for the *Akkermansia muciniphila* EB-AMDK19 strain of the present invention and the *Akkermansia muciniphila* ATCC BAA-835 strain.

To verify the safety of the *Akkermansia muciniphila* EB-AMDK19 strain isolated as described above, whether the strain has hemolytic activity and cytotoxicity was evaluated. To examine whether the strain has hemolytic activity, the strain was cultured using a blood agar medium prepared by adding 5% w/v defibrinated sheep blood to tryptic soy agar (17.0 g/L pancreatic digest of casein, 3.0 g/L pancreatic digest of soybean, 2.5 g/L dextrose, 5.0 g/L sodium chloride, 2.5 g/L potassium phosphate, 15 g/L agar), and the results are shown in FIG. 5. As can be seen in FIG. 5, it was confirmed that the *Akkermansia muciniphila* EB-AMDK19 strain of the present invention did not show a completely transparent part around the colony, suggesting that the strain does not cause β-hemolysis associated with pathogenicity.

In addition, in order to examine the strain has cytotoxicity, HT29 and Caco-2 cells, which are human colonic epithelial cells, were treated with the *Akkermansia muciniphila* EB-AMDK19 strain, and the viability of the cells was analyzed according to 3-(4,5-dimethyl-thiazol-2-yl)-2,5-diphenyltetrazolium bromide (MTT) assay, and the results are shown in FIG. 6. As can be seen in FIG. 6, it was confirmed that the *Akkermansia muciniphila* EB-AMDK19 strain did not affect the viability of the colonic epithelial cells, indicating that the strain has no cytotoxicity.

Example 3: Confirmation of Effect of *Akkermansia muciniphila* Strain on Treatment of Atopic Disease

3.1. Strain Sample

The *Akkermansia muciniphila* ATCC BAA-835 strain and *Akkermansia muciniphila* EB-AMDK19 live bacteria used in this experiment were prepared at a concentration of 1×10$^8$ CFU/150 µl PBS (25% glycerol, 0.05% cysteine/PBS).

15

3.2. Animal Model and Sampling

To observe atopic dermatitis lesions, 6-week-old NC/Nga mice (weighed about 21 to 25 g, SLC, Inc., Japan) were purchased from Daehan Biolink Co., Ltd. (Chungbuk, Korea). Animal tests were carried out in accordance with the Animal use and Care Protocol of the Institutional Animal Care and Use Committee (IACUC). The animals were acclimated for one week, and then raised for 9 weeks at a constant temperature of 22° C. and a relative humidity of 50 to 60% with a 12-hr light/12-hr dark cycle.

3.3. Induction of Atopic Dermatitis

The backs of 6-week-old NC/Nga mice were shaved clean, and then left to stand for 24 hours so that fine wounds of the skin were healed. 1% 2,4-dinitrochlorobenzene (DNCB) solution (Sigma-Aldrich Korea) was applied to the back of each mouse twice a week for 3 weeks to induce an immune response, and then 0.5% DNCB solution was applied twice a week to induce contact dermatitis. DNCB used in this Example was diluted at 0.5% and 1% in a solution obtained by mixing acetone and olive oil at 3:1.

Each of the corresponding drugs was administered orally daily for 6 weeks after induction of atopic dermatitis. As a positive control, dexamethasone was diluted with distilled water to a concentration of 60 µg/ml and administered orally in an amount of 200 µl daily (See Table 8).

TABLE 8

| Group | Administration group | Drug administered |
|---|---|---|
| Group I | Normal group | PBS |
| Group II | Atopic dermatitis control group (DNCB-induced atopic dermatitis) | PBS |
| Group III | ATCC BAA-835 strain-administered group | BAA-835 live bacteria, $1 \times 10^8$ CFU |
| Group IV | EB-AMDK19 strain-administered group | EB-AMDK19 live bacteria, $1 \times 10^8$ CFU |
| Group V | Positive control group (dexamethasone-administered group) | 60 µg/mℓ, 200 µℓ |

3.4. Evaluation of Atopic Dermatitis

After atopic dermatitis was induced by DNCB, treatment was performed by administering a preparation containing each of dexamethasone (DEX), the ATCC BAA-835 strain and the EB-AMDK19 strain for 6 weeks. To examine the clinical symptoms, the skin condition and the dermatitis score obtained by scoring the same were checked. Sensory evaluation was performed using a modification of the SCO-RAD (Scoring Atopic Dermatitis) index which is a clinical visual evaluation method which is commonly used for atopic dermatitis. Skin dryness, edema, erythema/hemorrhage, and erosion/excoriation were scored as follows: no symptoms=0, weak symptoms=1, moderate symptoms=2, and severe symptoms=3. Evaluation was performed every week, and the evaluation results are shown in FIGS. 7 and 8.

As a result of measuring the dermatitis score by visually observing the skin condition of each group during the 6-week treatment period, it could be confirmed that, in the atopic dermatitis-induced group (DNCB), the symptoms of atopic dermatitis were maintained for 6 weeks, whereas, in the experimental groups to which each of the ATCC BAA-835 strain, the EB-AMDK19 strain and dexamethasone (DEX) was administered, the symptoms of atopic dermatitis significantly decreased. In particular, it was shown that the group to which the *Akkermansia muciniphila* ATCC BAA-835 strain was administered and the group to which the EB-AMDK19 administration group of the present invention was administered had a better effect on the amelioration of atopic dermatitis than the positive control group to which dexamethasone was administered. In particular, it was confirmed that the group to which the EB-AMDK19 strain of the present invention was administered exhibited a better effect on the amelioration of the atopic skin condition than the *Akkermansia muciniphila* ATCC BAA-835 strain was administered. As a result of numerical evaluation based on the dermatitis score at week 6, it could be confirmed that decreases in dermatitis score of 38.4, 45.6 and 61.7% for 6 weeks compared to the atopic dermatitis-induced group appeared in the positive control group (DEX) (P=0.003), the ATCC BAA-835-administered group (P=0.009) and the EB-AMDK19-administered group (P<0.001), respectively.

3.5. Effect of Strain on Ear Edema Caused by Atopic Dermatitis

After severe atopic dermatitis was induced, the mice after completion of the experiment were sacrificed by anesthetizing with $CO_2$, and then the degree of edema of both ears was measured by the velocity transformation technique using a thickness gauge (Digimatic thickness gauge, 547-301, Mitu-toyo, Japan). The results of the measurement are shown in FIGS. 9 and 10.

Ear edema in the NC/Nga mice at 6 weeks was 0.55 mm in the normal group, 1.50 mm in the atopic dermatitis-induced group, 1.09 mm in the ATCC BAA-835-administered group (P<0.001), 0.87 mm in the EB-AMDK19-administered group (P<0.001), and 1.00 mm in the positive control group (DEX) (P<0.001). It was confirmed that the group to which the EB-AMDK19 of the present invention was administered showed a more significant effect of reducing ear edema than the positive control group. Moreover, it was confirmed that ear edema in the group to which the *Akkermansia muciniphila* EB-AMDK19 was administered significantly decreased (P=0.04) compared to that in the group to which the *Akkermansia muciniphila* ATCC BAA-835 was administered. Accordingly, it was confirmed that the pharmaceutical composition of the present invention had a remarkable effect of inhibiting edema in the atopic dermatitis-induced mouse model.

3.6. Measurement of Scratching Score

The day before the end of the experiment, the frequency of scratching the affected area due to itching was measured. For measurement of the frequency of scratching, each mouse was acclimated for 10 minutes, and then the frequency of scratching for 10 minutes was measured using a counter.

Referring to FIG. 11, the atopic dermatitis-induced group showed a significantly increased frequency of scratching (P<0.001) compared to the normal group. It was confirmed that the frequencies of scratching in the group to which the *Akkermansia muciniphila* ATCC BAA-835 was administered and the group to which the *Akkermansia muciniphila* EB-AMDK19 of the present invention was administered decreased by 66.7% (P=0.01) and 72.9% (P=0.005), respectively, compared to that in the atopic dermatitis-induced group. The positive control group showed a decrease in scratching frequency of about 59.4% (P=0.03) compared to the atopic dermatitis-induced group. Therefore, it was confirmed that the group to which the *Akkermansia muciniphila* EB-AMDK19 of the present invention was administered showed a better antipruritic effect than the positive control group to which dexamethasone was administered or the group to which the *Akkermansia muciniphila* ATCC BAA-835 was administered.

3.7. Measurement of Spleen Weight and Size

The spleen exhibits the characteristics of both primary and secondary lymphoid organs, is composed of a red pulp that filters red blood cells and a white pulp that exhibits humoral and cellular immunity, and is another important organ for immune responses (Mebius, R E and Kraal, G 2005 Structure and function of the spleen Nat Rev Immunol 5, pp 606-616). In addition, the spleen is where the final stage of B cell development occurs, and at the same time, the spleen functions as a specialized organ that responds to antigens derived from blood (Boehem, T and Bleul, CC 2007 The evolutionary history of lymphoid organs Nat Immunol 8, 131-135). The response of atopic dermatitis may induce various responses in the immune system, and these responses may primarily affect the weight of the spleen that is an immune organ.

Thus, the weight of the spleen was measured to observe the effect of the composition for preventing atopic dermatitis on the immune organs of NC/Nga mice with atopic dermatitis induced by DNCB. More specifically, after completion of the experiment, the experimental animals were anesthetized with $CO_2$ and sacrificed by cervical dislocation, and the abdomens thereof were opened, and spleen tissues were collected. The collected spleen tissues were washed with physiological saline, and then the sizes thereof were visually observed and the weights thereof were measured using a microbalance. The results are shown in FIGS. 12 and 13.

The spleen weight of the atopic dermatitis-induced group (DNCB) increased about 2 times compared to the normal group (P<0.001), and the ATCC BAA-835-administered group, the EB-AMDK19-administered group and the positive control group (DEX) showed decreases in spleen weight of 6.9%, 24.3% (P=0.03) and 23.3%, respectively, compared to the atopic dermatitis-induced group. In particular, the group to which the EB-AMDK19 strain of the present invention showed a better effect than the positive control group to which dexamethasone was administered, and also showed a greater decrease in spleen weight than the type strain ATCC BAA-835. Therefore, it was confirmed that the EB-AMDK19 of the present invention has the best immunosuppressive effect.

3.8. Measurement of Serum IgE Concentration

At the end of the experiment, each of the mice was anesthetized with $CO_2$ and blood was collected by cardiac puncture. The collected blood was centrifuged at 10,000 rpm for 5 minutes to separate the serum, and the serum IgE concentration was measured. The results of the measurement are shown in FIG. 14. The IgE concentration measurement was performed using an ELISA kit (IgE mouse uncoated ELISA kit cat #88-50460, Invitrogen, CA, USA).

Referring to FIG. 14, the serum IgE concentration in the control group treated with DNCB increased (1545.08 ng/ml, about 13-fold increase, P<0.001) compared to that in the normal group, but the serum IgE concentrations in the group to which the *Akkermansia muciniphila* ATCC BAA-835 was administered and the group to which the *Akkermansia muciniphila* EB-AMDK19 strain of the present invention was administered significantly decreased compared to that in the atopic dermatitis-induced group. It was confirmed that the serum IgE concentrations in the ATCC BAA-835 group, the EB-AMDK19 group and the positive control groups significantly decreased to 13043.6 ng/ml (34.95% decrease), 7571.64 ng/ml (62.24% decrease), and 11891.34 ng/ml (40.70% decrease), respectively, compared to that in the atopic dermatitis-induced group (P<0.001). In particular, the serum IgE concentration in the group to which the EB-AMDK19 strain of the present invention was 41.95% (P=0.007) lower than that in the group to which the type strain *Akkermansia muciniphila* ATCC BAA-835 was administered, and was 36.32% (P=0.05) lower than that in the positive control group. Therefore, it was confirmed that the composition containing the EB-AMDK19 strain of the present invention has a significantly excellent effect of inhibiting IgE production, and is most effective in alleviating atopic symptoms.

3.9. Histopathological Observation

At the end of the experiment, each of the mice was sacrificed, and the skin was isolated, fixed in 10% formaldehyde solution, and embedded in paraffin, and the paraffin block was sectioned. The paraffin sections were stained with hematoxylin & eosin (H&E) and changes in the thicknesses of the epidermal layer and the dermal layer were observed with an optical microscope at 200× magnification. The results are shown in FIG. 15. Hyperkeratosis and epithelial hyperplasia were histologically graded as follows: the thickness of the normal group=0; 2 times the thickness of the normal group=1; 3 times=2; 4 times=3; and 4 times or more=4. The results are shown in FIGS. 15(B) and 15(C).

As a result of observing the back skin tissue of the NC/Nga mice by H&E staining, as shown in FIG. 15, the atopic dermatitis-induced group (DNCB) showed thickening of the epidermal layer toward the dermal layer, and histopathological findings, including severe damage to the skin barrier and increased infiltration of inflammatory cells, compared to the atopic dermatitis-induced group (DNCB). In addition, microscopic observation indicated that all the *Akkermansia muciniphila*-administered groups and the positive control group (DEX group) all showed histopathological features similar to those of the normal group, because they showed decreased infiltration of inflammatory cells, and thickening of both the epidermal layer and the dermal layer therein, which is observed upon induction of atopic dermatitis, was inhibited.

As shown in the graphs of FIGS. 15(B) and 15(C), it was confirmed that hyperkeratosis and epithelial hyperplasia significantly increased in the atopic dermatitis-induced group (DNCB) compared to the normal group, and were significantly inhibited in the positive control group, the group to which the *Akkermansia muciniphila* ATCC BAA-835 was administered and the group to which the *Akkermansia muciniphila* EB-AMDK19 of the present invention was administered, compared to the atopic dermatitis-induced group (DNCB).

3.10. Observation of Body Weight Change

To examine whether a change in body weight occurs due to the strain used in this experiment, the body weights of the experimental animals were measured weekly during the strain administration period including the atopic dermatitis induction period. As shown in FIG. 16, as a result of measuring the body weight at 6 weeks of administration of the strain, it was confirmed that, in the atopic dermatitis-induced group (DNCB), body weight loss occurred due to side effects of the drug and stress. On the other hand, the body weights of the groups to which the *Akkermansia muciniphila* strains were administered tended to increase compared to that of the atopic dermatitis-induced group. In addition, it could be confirmed that the body weight losses in the groups to which the *Akkermansia muciniphila* strains (type strain ATCC BAA-835 and EB-AMDK19) were administered were inhibited compared to that in the positive control group to which dexamethasone, a steroid-based treatment, was administered. Particularly, it was confirmed that administration of the EB-AMDK19 strain of the present invention showed the same pattern of weight gain as that of the normal group, indicating that the EB-AMDK19 strain does not show a side effect of weight loss and thus is safe.

3.11. Measurement of Serum Cytokine Concentrations

After induction of atopic dermatitis, the concentrations of cytokines related to Th1 and Th2 were measured to examine the immune response resulting from administration of the *Akkermansia muciniphila* EB-AMDK19 strain of the present invention. For statistics for all experiments, one-way ANOVA was performed using GraphPad Prism 7.04.

At the end of the experiment, the mice were anesthetized with $CO_2$, and blood was collected by cardiac puncture. The collected blood was centrifuged at 10,000 rpm for 10 minutes, and the serum was separated and stored at $-80°$ C. The concentrations of IL-4, IL-12, IFN-$\gamma$ and IL-6 cytokines were measured using an ELISA kit (Invitrogen, CA, USA), and the results of the measurement are shown in FIGS. 17(A), 17(B), 18(A), and 18(B).

First, the concentrations of the cytokines IL-4 and IL-6, which are induced by Th2 cell activity and also known as indicators of inflammatory response, were examined. As shown in FIG. 17(A), the IL-4 concentration was significantly higher in the atopic dermatitis-induced group than in the normal group (P=0.03), and significantly decreased in all the positive control group (DEX) and the group to which the *Akkermansia muciniphila* ATCC BAA-835 was administered and the group to which the *Akkermansia muciniphila* EB-AMDK19 was administered, compared to that in the atopic dermatitis-induced group. In particular, it was shown that the IL-4 concentration in the EB-AMDK19-administered group (P=0.001) significantly decreased compared to that in the ATCC BAA-835-administered group (P=0.03). In addition, it could be confirmed that the results for the concentration of IL-6 were also similar to those for the IL-4 concentration (see FIG. 17(B)). As a result of measuring the IL-6 concentration, it could be confirmed that the IL-6 concentration increased 43.4% (P=0.03) in the atopic dermatitis-induced group, and was inhibited in the positive control group (DEX) and the *Akkermansia muciniphila*-administered groups (DEX: P=0.03, ATCC BAA-835: P=0.04, and EB-AMDK19: P=0.006) compared to the atopic dermatitis-induced group (DNCB). It was confirmed that the concentration of IL-6 was 30.5% lower in the ATCC BAA-835-administered group than in the atopic dermatitis-induced group (DNCB) and was 39.4% lower in the EB-AMDK19-administered group. Thus, cytokines such as IL-4 and IL-6 activate humoral immunity and activate B-cells to increase IgE, causing atopic dermatitis, and it is believed that the EB-AMDK19 strain of the present invention effectively inhibit cytokines compared to the type strain ATCC BAA-835.

3.12. Effect of EB-AMDK19 Strain on Blood Th1 Cytokines, IFN-$\gamma$ and IL-12

In this experiment, the Th1 cytokine IFN-$\gamma$ and its inducer IL-12 were measured. As a result, as shown in FIGS. 18(A) and 18(B), it was confirmed that these cytokines all significantly increased in the EB-AMDK19-administered group. IFN-$\gamma$ significantly increased in the EB-AMDK19-administered group (P=0.001) compared to the atopic dermatitis-induced group (P<0.001), the positive control group (DEX) (P=0.007) and the type strain *Akkermansia muciniphila* ATCC BAA-835-administered group (P<0.001). In addition, the concentration of IL-12 significantly decreased in the atopic dermatitis-induced group compared to the normal group (P=0.008) and significantly increased in the EB-AMDK19-administered group (P<0.001). The concentration of IL-12 significantly increased in the positive control group (DEX) (P=0.001), the type strain *Akkermansia muciniphila* ATCC BAA-835 group (P=0.006) and the EB-AMDK19 group (P<0.001) compared to the atopic dermatitis-induced group (DNCB). In particular, it was confirmed that the concentration of IL-12 in the EB-AMDK19-administered group significantly increased compared to that in the positive control group (DEX) (P=0.02) and also significantly increased compared to that in the type strain ATCC BAA-835 group (P<0.001). Therefore, it was confirmed that administration of the EB-AMDK19 strain of the present invention results in an increase in serum IL-12 and IFN-$\gamma$ concentrations and thus induces Th1 differentiation.

3.13. Effect of Administration of EB-AMDK19 Strain on Production of Th1 and Th2 Cytokines in Atopic Dermatitis Animal Model From an immunological point of view, atopic dermatitis is a disease caused by an excessive imbalance between Th1 and Th2 immune responses. Thus, the cytokine concentrations measured as described above were expressed as the ratio of Th2/Th1 cytokines, and the results are shown in FIGS. 19(A), 19(B), 20(A), and 20(B).

Figures 19A, 19B:
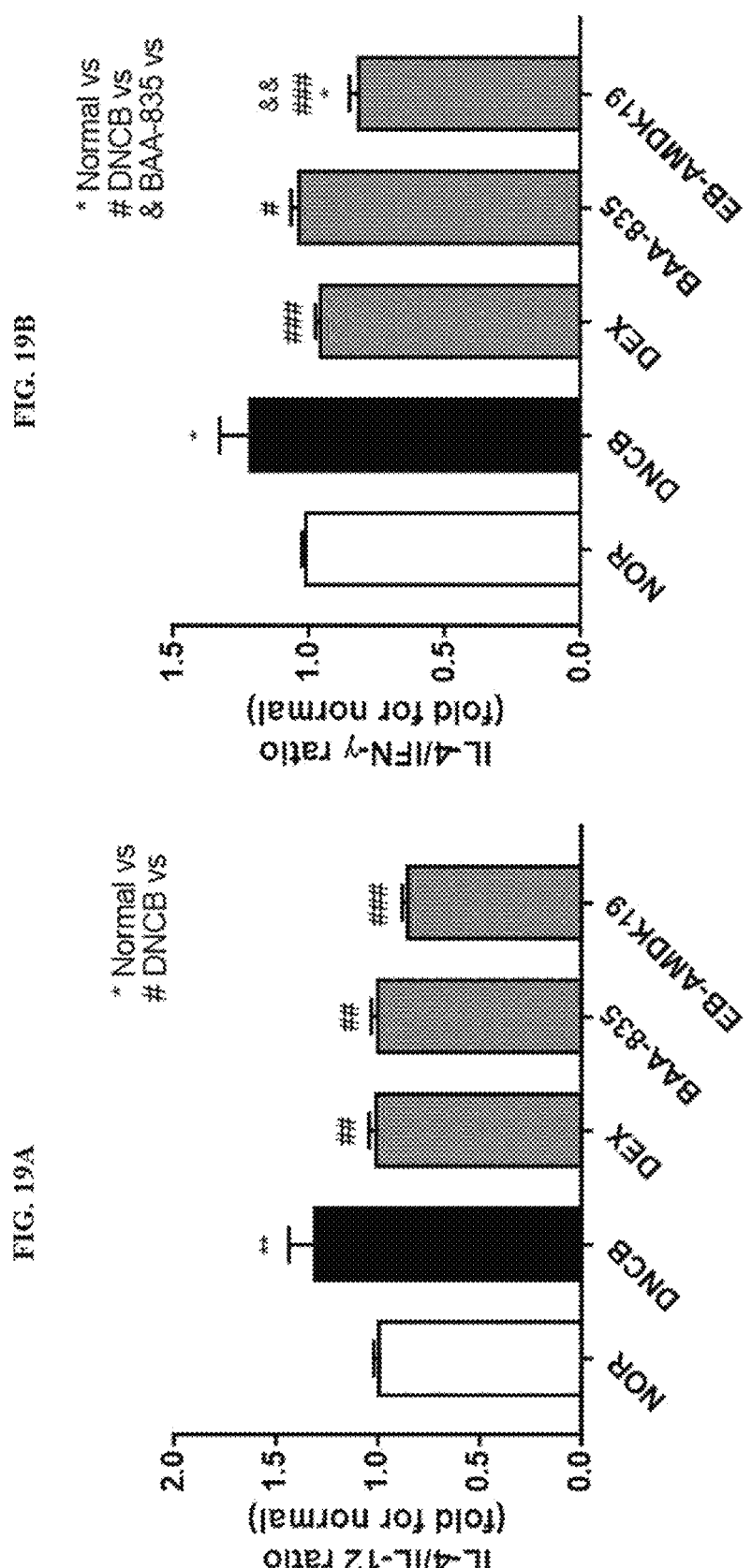

Referring to FIG. 19(A), as a result of analyzing the IL-4/IL-12 ratio, it was confirmed that, in the atopic dermatitis-induced group (DNCB), the IL-4/IL-12 ratio significantly increased (P=0.006), indicating an increase in Th2 cytokine that typically appears in atopic dermatitis. In addition, it was confirmed that the IL-4/IL-12 ratio significantly decreased in all the positive control group, the type strain *Akkermansia muciniphila* ATCC BAA-835-administered group and the *Akkermansia muciniphila* EB-AMDK19-administered group (DEX: P=0.006, ATCC BAA-835: P=0.003, and EB-AMDK19: P<0.001) compared to the atopic dermatitis-induced group (DNCB). In addition, the same pattern could also be confirmed for the IL-4/IFN-$\gamma$ ratio (see FIG. 19(B)). It could be confirmed that the ratio of IL-4/IFN-$\gamma$ decreased 15.0% (P=0.03) in the ATCC BAA-835-administered group and 32.9% (P<0.001) in the EB-AMDK19-administered group compared to the DNCB group. In particular, it could be confirmed that the ratio of IL-4/IFN-$\gamma$ significantly decreased in the EB-AMDK19-administered group compared to the ATCC BAA-835-administered group (see FIG. 19(B)).

In addition, it could be confirmed that the results for the ratio of IL-6/IL-12 and the ratio of IL-6/IFN-$\gamma$ were similar to the above-described results. It was confirmed that the ratio of IL-6/IL-12 was 1.5-fold higher (P=0.01) in the atopic dermatitis-induced group than in the normal group, and decreased 34.5% (P=0.02), 35.9% (P=0.005) and 50.5% (P<0.001) in the positive control group, the ATCC BAA-835-administered group and the EB-AMDK19-administered group, respectively, compared to the atopic dermatitis-induced group. The IL-6/IFN-$\gamma$ ratio also increased 14% (P=0.004) in the atopic dermatitis-induced group compared to the normal group, and decreased 12.7% (P=0.01) in the positive control group and 27.0% (P<0.001) in the EB-AMDK19-administered group compared to the atopic dermatitis-induced group. The IL-6/IFN-$\gamma$ ratio in the EB-AMDK19-administered group was significantly lower than that in the positive control group or the *Akkermansia muciniphila* ATCC BAA-835-administered group.

As described above, the pharmaceutical composition for preventing or treating atopic disease containing, as an active ingredient, the EB-AMDK19 strain (*Akkermansia muciniphila* EB-AMDK19) according to the present invention, inhibits the production of the Th2 cytokines IL-4 and IL-6, resulting in inhibition of excessive production of IgE, exhibits an excellent effect of treating atopic disease by promoting production of the Th1 cytokines IFN-$\gamma$ and IL-12. In particular, the pharmaceutical composition significantly overcomes the limitations of conventional probiotic preparations, and exhibits a preventive, ameliorative or therapeutic effect against atopic dermatitis at the same level as that of steroid-based drugs. Therefore, the pharmaceutical composition is highly industrially applicable.

The specific examples described herein serve merely to illustrate preferred embodiments of the present invention and should not be construed as limiting the present invention. Those skilled in the art may be embodied in various modified or changed forms without departing from the spirit and scope of the present invention. Therefore, the scope of protection of the present invention should be defined by the attached claims, and various modifications and changes as described above are intended to fall within the scope of protection of the present invention.

ACCESSION NUMBER

Depository Authority: Korean Collection for Type Cultures
Accession Number: KCTC13761BP
Deposit Date: Dec. 5, 2018

The invention claimed is:

1. A method for alleviating or ameliorating asthma, atopic dermatitis, urticaria, or allergic rhinitis in a subject in need thereof, comprising administering a composition comprising an *Akkermansia muciniphila* EB-AMDK19 strain (KCTC13761BP) as an active ingredient.

2. The method of claim 1, wherein the *Akkermansia muciniphila* EB-AMDK19 strain comprises the 16s rRNA sequence of SEQ ID NO: 1.

3. The method of claim 1, wherein the *Akkermansia muciniphila* EB-AMDK19 strain is live or pasteurized.

4. The method of claim 1, wherein the composition further comprises a vitamin or an immunosuppressant.

5. The method of claim 4, wherein the immunosuppressant is selected from the group consisting of a glucocorticoid, cyclosporine, tacrolimus, pimecrolimus, ISA(TX)247, rapamycin, a Type IV phosphodiesterase (PDE) inhibitor, mycophenolate mofetil, and dexamethasone.

6. The method of claim 4, wherein the composition further comprises the immunosuppressant, wherein said immunosuppressant is a calcineurin inhibitor.

7. The method of claim 1, wherein the composition comprises the *Akkermansia muciniphila* EB-AMDK19 strain as the active ingredient in an amount of $10^8$ to $10^{12}$ CFU, or comprises a culture product having $10^8$ to $10^{12}$ CFU of live or pasteurized *Akkermansia muciniphila* EB-AMDK19 strain.

8. The method of claim 1, wherein the composition is a pharmaceutical composition, a foodstuff, or a dietary supplement.

9. The method of claim 1, wherein the atopic dermatitis is skin allergy, skin urticaria, or psoriasis.

10. The method of claim 1, wherein the administration of the composition increases a level of IFN-$\gamma$ in blood compared to a level of IFN-$\gamma$ before the administration.

11. The method of claim 1, wherein administration of the composition decreases a ratio of an amount of IL-6 to an amount of IFN-$\gamma$ in blood compared to a ratio of an amount of IL-6 to an amount of IFN-$\gamma$ before the administration.

12. The method of claim 1, wherein said atopic dermatitis is hyperkeratosis, hyperplasia, lichenification, or itching.

\* \* \* \* \*